US012781250B2

(12) United States Patent
Sauer et al.

(10) Patent No.: US 12,781,250 B2
(45) Date of Patent: Nov. 3, 2026

(54) METHODS FOR PRODUCING HIGHLY PURIFIED (R)-3'-HYDROXYBUTYL (R)-3'-HYDROXYBUTYRATE AND USE FOR ENHANCING BODILY FUNCTION AND TREATING DISEASE STATES

(71) Applicant: Romeo Tango, LLC, Newark, DE (US)

(72) Inventors: Daryl Richard Sauer, Trevor, WI (US); Carl Edward Sheeley, Jr., Racine, WI (US)

(73) Assignee: Aurelion Bioscience, LLC, Glen Ellyn, IL (US)

( * ) Notice: Subject to any disclaimer, the term of this patent is extended or adjusted under 35 U.S.C. 154(b) by 0 days.

(21) Appl. No.: 19/347,997

(22) Filed: Oct. 2, 2025

(65) Prior Publication Data

US 2026/0098281 A1 Apr. 9, 2026

Related U.S. Application Data

(60) Provisional application No. 63/703,691, filed on Oct. 4, 2024.

(51) Int. Cl.

| | |
|---|---|
| ***C12P 7/62*** | (2022.01) |
| ***A61K 31/22*** | (2006.01) |
| ***C12N 9/18*** | (2006.01) |
| ***C12N 11/087*** | (2020.01) |
| ***G01N 30/02*** | (2006.01) |
| ***G01N 30/72*** | (2006.01) |

(52) U.S. Cl.

CPC ................ *C12P 7/62* (2013.01); *A61K 31/22* (2013.01); *C12N 9/18* (2013.01); *C12N 11/087* (2020.01); *C12Y 301/01003* (2013.01); *G01N 30/72* (2013.01); *G01N 2030/025* (2013.01)

(58) Field of Classification Search

None

See application file for complete search history.

(56) References Cited

U.S. PATENT DOCUMENTS

| | | | | |
|---|---|---|---|---|
| 2011/0237666 | A1 * | 9/2011 | Clarke | A61K 31/22 560/179 |
| 2012/0064611 | A1 | 3/2012 | Robertson et al. | |
| 2014/0308719 | A1 | 10/2014 | Clarke et al. | |
| 2015/0065571 | A1 | 3/2015 | Clarke et al. | |
| 2020/0113220 | A1 | 4/2020 | Clarke | |
| 2021/0094900 | A1 * | 4/2021 | Ulrich | A61P 3/04 |
| 2024/0018491 | A1 * | 1/2024 | Basheer | C12N 11/02 |
| 2024/0317671 | A1 | 9/2024 | Ulrich | |

OTHER PUBLICATIONS

Chica et al. Curr Opin Biotechnol. Aug. 2005;16(4):378-84. (Year: 2005).*

Singh et al. Curr Protein Pept Sci. 2017, 18, 1-11 (Year: 2017).*

* cited by examiner

*Primary Examiner* — Christian L Fronda

(74) *Attorney, Agent, or Firm* — Tracnik Law, PLLC; Joseph P Kincart

(57) ABSTRACT

The present disclosure relates to highly purified (R)-3'-hydroxybutyl (R)-3'-hydroxybutyrate and biomedical uses thereof. In particular highly purified (R)-3'-hydroxybutyl (R)-3'-hydroxybutyrate, is provided for enhancing bodily function and treating various disease states. The methods described herein provide for production of a highly purified (R)-3'-hydroxybutyl (R)-3'-hydroxybutyrate via processes external to the human body and administering effective amounts of highly purified (R)-3'-hydroxybutyl (R)-3'-hydroxybutyrate to human subjects to achieve a range of therapeutic benefits, including but not limited to, one or more of: inhibiting inflammasome activation, reducing pro-inflammatory cytokines, improving insulin sensitivity, enhancing mitochondrial biogenesis, and promoting muscle protein synthesis. Additionally, highly purified (R)-3'-hydroxybutyl (R)-3'-hydroxybutyrate is administered in an amount and frequency conducive to one or more of: improving cognitive function, reducing oxidative stress, enhancing cardiovascular health, and supporting neuroprotection. Methods for manufacturing and purifying (R)-3'-hydroxybutyl (R)-3'-hydroxybutyrate compositions to ensure high specificity and efficacy in therapeutic applications are also provided.

17 Claims, 4 Drawing Sheets

METHODS FOR PRODUCING HIGHLY PURIFIED (R)-3'-HYDROXYBUTYL (R)-3'-HYDROXYBUTYRATE AND USE FOR ENHANCING BODILY FUNCTION AND TREATING DISEASE STATES

CROSS REFERENCE TO RELATED MATTERS

This application claims the benefit of priority to U.S. Provisional Ser. No. 63/703,691, filed on Oct. 4, 2024, the entire contents of which are incorporated herein by reference.

FIELD OF THE INVENTION

The present disclosure relates to biomedical and nutritional uses of enantiomerically purified ketone bodies and ketone esters, particularly (R)-3'-hydroxybutyl (R)-3'-hydroxybutyrate, for enhancing bodily function and treating disease states such as in relationship to cognitive function, muscle power output, inflammation reduction, metabolic disorders, and mitochondrial function and methods of producing purified ketone bodies and ketone esters.

BACKGROUND

The background related to production of (R)-3-hydroxybutyrate (BHB-herein) related compounds and associated uses may be summarized in the following patent applications the contents of each of which are incorporated herein by reference: Process for Producing (R)-3-hydroxybutyl (R)-3-hydroxybutyrate, K Clarke, R L Veech & M T King, WO2014/140308 A1; Ketone Body and Ketone Body Ester for Reducing Muscle Breakdown, K Clarke & P Cox, WO2015/018913 A1; Process for Producing (R)-3-hydroxybutyl-3-hydroxybutyrateate, K Clarke, R L Veech & MT King, WO2014/140308 A1; Preparation of (3R)-hydroxybutyl-(3R)-hydroxybutyrate by Enzymatic Enatioselective Reduction, K Clarke, J Robertson & R L Veech, WO2010/120300 A1; and Compounds for Use in Reducing Liver Fat, K Clarke, WO2019/002828A1.

SUMMARY

The present invention leverages highly purified (R)-3'-hydroxybutyl (R)-3'-hydroxybutyrate for the unique biochemical properties of metabolically generated BHB to modulate metabolic pathways, gene expression, and cellular signaling, thereby offering a comprehensive approach to improving health and treating diseases such as metabolic disorders, neurodegenerative diseases, cardiovascular conditions, and inflammatory diseases.

In some examples, BHB may be sourced to the body through ingestion of highly purified (R)-3'-hydroxybutyl (R)-3'-hydroxybutyrate (also referred to herein as R, R BHB-BDO ester). As discussed in more detail in following sections, ingestion of R, R BHB-BDO ester may be processed by various processes in the body to generate R-BHB and R-BDO. Subsequently R-BDO may be metabolically processed to also yield R-BHB. Accordingly, methods to produce isomerically pure R, R BHB-BDO esters are important to afford highly pure R-BHB for clinical/medicinal purposes.

Enantiomerically purified ketone bodies and ketone esters ingested for biomedical and nutritional uses may be provided for administration to a human subject in amount and frequency conducive to enabling the beneficial biological response. In particular, in some embodiments, highly purified (R)-3'-hydroxybutyl (R)-3'-hydroxybutyrate may be provided for enhancing bodily function and treating various disease states. The methods described herein provide for production of a pure form of (R)-3'-hydroxybutyl (R)-3'-hydroxybutyrate via processes external to the human body.

In some methods, steps may include administering effective amounts of highly purified (R)-3'-hydroxybutyl (R)-3'-hydroxybutyrate to human subjects to achieve a range of therapeutic benefits, including but not limited to one or more of: inhibiting inflammasome activation, reducing pro-inflammatory cytokines, improving insulin sensitivity, enhancing mitochondrial biogenesis, and promoting muscle protein synthesis. Additionally, the present disclosure provides for highly purified (R)-3'-hydroxybutyl (R)-3'-hydroxybutyrate administration in an amount and frequency conducive to one or more of: improving cognitive function, reducing oxidative stress, enhancing cardiovascular health, and supporting neuroprotection. The disclosure further includes methods for manufacturing and purifying (R)-3'-hydroxybutyl (R)-3'-hydroxybutyrate to ensure high specificity and efficacy in therapeutic applications.

As mentioned, when ingested (R)-3'-hydroxybutyl (R)-3'-hydroxybutyrate may be metabolized in various manners to yield R-BHB in a user's blood stream. Herein, the acronym BHB will be reserved to mean the same as R-BHB, wherefore compositions including the S-BHB enantiomer will include the indication of the S prefix. R-BHB is a versatile and vital energy molecule that supports metabolic processes across various animal species, especially during times when glucose is not available or is in limited supply.

In humans, the stereoisomer (R) β-hydroxybutyrate which may also be called D β-hydroxybutyrate and herein BHB is synthesized in the liver from fatty acids, β-hydroxy β-methylbutyrate, and ketogenic amino acids, primarily during periods of low carbohydrate intake. In some examples, this process may start with the production of acetoacetate, which may then be converted into BHB by the enzyme β-hydroxybutyrate dehydrogenase. BHB may also be produced through an alternative pathway involving butyrate metabolism, where it undergoes several conversions before being formed.

During ketosis, the concentration of BHB in the blood increases, providing an essential energy source for the brain and muscles when glucose is scarce. The physiological effects of BHB ingestion include reduced appetite, increased endurance, and improved mental clarity, though responses may vary based on individual factors.

Ingested (R)-3'-hydroxybutyl (R)-3'-hydroxybutyrate supplements may be metabolized in the gastrointestinal tract and subsequently may be rapidly absorbed into the bloodstream, with generated BHB crossing the blood-brain barrier to sustain cognitive function and promote energy efficiency by shifting the body's fuel use from glucose to ketones and fatty acids.

In some examples, the generated BHB may influence metabolic signaling pathways, inhibiting histone deacetylases (HDACs) to modulate gene expression, potentially offering anti-inflammatory and antioxidant benefits. Additionally, BHB may enhance mitochondrial function and stimulate the production of proteins linked to stress resistance, longevity, and overall metabolic health.

Despite its benefits, some methods of providing BHB supplementation may cause side effects such as gastrointestinal discomfort, electrolyte imbalances, and potential kidney stress, especially with high doses or prolonged use. As described herein, methods for highly purified and isomerically pure (R)-3'-hydroxybutyl (R)-3'-hydroxybutyrate are utilized for improved effectiveness and lowered side effect profiles. With this perspective in mind, it may be noted that uses of purified (R)-3'-hydroxybutyl (R)-3'-hydroxybutyrate may involve the ingestion of between 80-200 gm per day. In more standard manufactured formulations for BHB supplementation, the various materials including examples such as 3-hydroxybutyl 3-hydroxybutyrate, may typically contain a mixture of the (R) and(S) enantiomers and in the case of the esters mixtures of (R)(R), (R)(S), (S)(R), and (S)(S) stereoisomers/enantiomers. With any of these molecules or other impurities related to the production of the monoester, relatively small levels of impurities may still result in a high exposure of those impurities relative to their side effect profile thresholds. Accordingly, unprecedented treatment protocols where levels of impurity exposure are dramatically reduced may offer novel overall treatment efficacy. In some examples, higher doses of the desired (R)-3'-hydroxybutyl (R)-3'-hydroxybutyrate may be dosed to patients based on the reduction or elimination of side effect causing impurities.

Referring now to FIGS. 1A-1K, stereochemical structures for the various isomers of potential relevance are illustrated. In FIG. 1A the focal moiety of the preset disclosure (R)-3'-hydroxybutyl (R)-3'-hydroxybutyrate 100 with the first (R) form chiral center 101 and the second (R) form chiral center 102 is illustrated. When this moiety is processed in the body of a user the initial products may include the structures illustrated in FIGS. 1B through 1D. Referring to FIG. 1B, BHB or (R)-3-hydroxybutyric acid 110 is illustrated with its (R) form chiral center 111 depicted. In the various environments within the cells and body structures of the user BHB may exist as the conjugate base (R)-3-hydroxybutyrate 120 which is illustrated with its (R) form chiral center 121. Proceeding to FIG. 1D, an initial metabolic product from (R)-3'-hydroxybutyl (R)-3'-hydroxybutyrate ingestion may also include (R)-1,3-butanediol 130. Its (R) form chiral center 131 is also illustrated.

In some examples, the(S) enantiomer(S) β-hydroxybutyrate or its ester isomers (S)(R), (R) (S) and (S)(S) 3-hydroxybutyl 3-hydroxybutyrate, may be a significant cause of some of the previously mentioned side effects. Proceeding to FIG. 1E, the (R)-3'-hydroxybutyl (S)-3'-hydroxybutyrate 140 stereoisomer is illustrated along with its chiral centers 141 and 142. Proceeding to FIG. 1F, the (S)-3'-hydroxybutyl (R)-3'-hydroxybutyrate 150 stereoisomer is illustrated along with its chiral centers 151 and 152. FIG. 1G, the (S)-3'-hydroxybutyl (S)-3'-hydroxybutyrate 160 stereoisomer is illustrated along with its chiral centers 161 and 162.

When any of these(S) form containing isomers (140,150 and 160) are metabolized the products may include (S)-3-hydroxybutyric acid 170 illustrated in FIG. 1H along with its chiral center 171. Similarly to the (R) form hydroxybutyric acid, the(S) form may exist as its conjugate base as illustrated in FIG. 1I, (S)-3-hydroxybutyrate 180 along with its chiral center 181. Similarly, as well the(S) form (S)-1,3-butanediol 190 is illustrated in FIG. 1J along with its chiral center 191. These various(S) form compounds may have a role in side effect profiles as mentioned previously.

Accordingly, the present disclosure describes methods of production of (R)-3'-hydroxybutyl (R)-3'-hydroxybutyrate supplies in highly purified forms. There are also descriptions of methods of purifying 3'-hydroxybutyl-3'-hydroxybutyrate supplies to generate enantiomerically pure forms, whether (R)(R) or (S)(S) forms. Moreover, in some examples herein, mixtures of (R)-3'-hydroxybutyl (R)-3'-hydroxybutyrate may be formed with other additives to ameliorate noted side effects.

Current processing alternatives for the production (R)-3-Hydroxybutyl (R)-3-Hydroxybutyrate result in formulations that are at best 80-85% pure for the desired enantiomer. Accordingly, there are numerous other isomers that may reduce the effectiveness and/or generate side effect profiles in standard processing. A key aspect of the instant application is to form highly purified (R)-3-Hydroxybutyl (R)-3-Hydroxybutyrate for its improvement in these respects. In some examples, highly purified (R)-3-Hydroxybutyl (R)-3-Hydroxybutyrate samples may be at least 95% pure. In some other examples, highly purified (R)-3-Hydroxybutyl (R)-3-Hydroxybutyrate samples may be at least 99% pure.

In some examples, a method for manufacturing a purified (R)-3'-hydroxybutyl (R)-3'-hydroxybutyrate may involve various techniques to ensure high specificity and efficiency in removing the undesired S-form stereoisomers including (R)(S), (S)(R), and (S)(S) stereoisomers/enantiomers. One approach, for example, may use an enzyme, possibly derived from a microbial source, that selectively targets and eliminates the S-form. In some other examples, another method may combine enzymatic steps with high-performance liquid chromatography (HPLC) for further purification. Additionally, a continuous flow reactor system with immobilized enzymes may be employed for scalable production, or a batch processing method may be used for small-scale or high-purity production. In some approaches, additional focus on the stereo-purity of starting materials is included. In still further approaches, careful optimization of process variables for processing steps may result in improved purity.

Isolates which have been enantiomerically purified may be formulated into various products that may be used to enhance bodily function or treat disease states, as described in detail in further sections of the present disclosure. In some examples, mixtures may be formulated using the purified (R)-3'-hydroxybutyl (R)-3'-hydroxybutyrate enantiomer. The mixtures may include compositions formed by adding controlled amounts of the (R)(S), (S)(R), and (S)(S) stereoisomers/enantiomers variously.

In some other examples, enantiomerically purified (R)-3'-hydroxybutyl (R)-3'-hydroxybutyrate may be mixed with other substances, as described in later sections, to reduce or modify the side effects of 3-hydroxybutyl-3-hydroxybutyrate ingestion as mentioned previously, including additions which may improve the palatability of the formulation. However, in some examples the purified isolate alone may be utilized.

According to one aspect of the present disclosure, a method for inhibiting NOD-like receptor family pyrin domain containing 3 (NLRP3) inflammasome activation in a subject may include administering an effective amount of the highly purified (R)-3'-hydroxybutyl (R)-3'-hydroxybutyrate to the subject. According to another aspect, the method may include examples wherein the inhibition of NLRP3 inflammasome activation reduces the secretion of pro-inflammatory cytokines IL-1β and IL-18. Furthermore, according to yet another aspect, a method may include examples for reducing IL-6 levels in a subject includes administering an effective amount of (R)-3'-hydroxybutyl (R)-3'-hydroxybutyrate to the subject, wherein the result of metabolism, BHB may activate the GPR109A receptor and inhibit NF-kB activity. According to another aspect, the method may include examples wherein the reduction of IL-6 levels is achieved through the antioxidative effects of BHB.

In some other examples, a method for inhibiting Tumor Necrosis Factor Alpha (TNF-alpha) production in a subject may include administering an effective amount of highly purified (R)-3'-hydroxybutyl (R)-3'-hydroxybutyrate to the subject, wherein generated BHB activates the GPR109A receptor and nuclear factor erythroid 2-related factor 2 (Nrf2) pathway. According to another aspect, the method may include examples wherein the inhibition of TNF-alpha production is achieved through the antioxidative effects of BHB.

According to yet another aspect, a method for increasing adenosine levels in a subject may include administering an effective amount of highly purified (R)-3'-hydroxybutyl (R)-3'-hydroxybutyrate to the subject, wherein the increased adenosine levels may exert anti-inflammatory effects via A1 and A2 receptors. According to another aspect, the method may include examples wherein the anti-inflammatory effects may include the reduction of IL-6 and TNF-alpha levels and the increase of IL-10 levels.

In some other examples, a method for promoting the polarization of macrophages towards the M2 phenotype in a subject includes administering an effective amount of highly purified (R)-3'-hydroxybutyl (R)-3'-hydroxybutyrate to the subject. In these examples, the BHB may inhibit histone deacetylases (HDACs) and activate the G-protein coupled receptor 109A (GPR109A) receptor. According to another aspect, the method may include examples wherein the M2 macrophage phenotype is associated with anti-inflammatory properties.

According to yet another aspect, a method for activating the mechanistic Target of Rapamycin Complex 1 (mTORC1) signaling pathway in a subject may include administering an effective amount of highly purified (R)-3'-hydroxybutyl (R)-3'-hydroxybutyrate to the subject, wherein the activation of mTORC1 promotes muscle protein synthesis. According to another aspect, the method may include examples wherein the activation of mTORC1 is indicated by the phosphorylation of p70S6 kinase (p70S6K) and eukaryotic translation initiation factor 4E-binding protein 1 (4E-BP1).

According to yet another aspect, a method for reducing systemic inflammation in a subject may include administering an effective amount of highly purified (R)-3'-hydroxybutyl (R)-3'-hydroxybutyrate to the subject, wherein BHB inhibits the NF-κB signaling pathway. According to another example, the method may include reduction of systemic inflammation that may occur in muscle wasting due to their association with chronic inflammation.

In some examples, a method for mitigating oxidative stress in a subject may include administering an effective amount of highly purified (R)-3'-hydroxybutyl (R)-3'-hydroxybutyrate to the subject, wherein BHB enhances the activity of antioxidant enzymes and reduces the production of reactive oxygen species (ROS). In some of these examples, the method may include examples wherein the mitigation of oxidative stress may be achieved through the activation of the Nrf2 pathway.

According to yet another aspect, a method for improving glucose management in a subject may include administering an effective amount of highly purified (R)-3'-hydroxybutyl (R)-3'-hydroxybutyrate to the subject, wherein BHB resulting from metabolism improves glucose control and reduces fructosamine levels. According to another aspect, the method may include examples wherein the improved glucose management is indicated by lower levels of Hemoglobin A1c (HbA1c) and Homeostasis Model Assessment of Insulin Resistance (HOMA-IR). In some examples, highly purified (R)-3'-hydroxybutyl (R)-3'-hydroxybutyrate may be combined with other pharmaceuticals in the formulation such as in non-limiting examples, metformin, diuretics and glucagon like protein-1 receptor agonists include but not limited to semaglutide, liraglutide, exenatide, dulaglutide, lixisenatide, albiglutide and efpeglenatide. In some other examples, BHB may be combined with dual glucagon like protein-1 receptor agonist and glucose-dependent insulinotropic polypeptide receptor agonist molecules such as tirzepatide.

According to yet another aspect, a method for protecting a subject against neurodegeneration may include administering an effective amount of highly purified (R)-3'-hydroxybutyl (R)-3'-hydroxybutyrate to the subject. In these examples, the metabolically produced BHB may serve as an alternative energy source for neurons. In some of these examples, the method may include cases wherein the protection against neurodegeneration is achieved through the reduction of oxidative stress, inhibition of neuroinflammation, enhancement of mitochondrial function, stimulation of autophagy, and regulation of apoptotic pathways.

In some examples, a method for enhancing cognitive function in a subject may include administering an effective amount of highly purified (R)-3'-hydroxybutyl (R)-3'-hydroxybutyrate to the subject.

According to another aspect, a method for improving cognitive performance in subjects with psychiatric conditions includes administering highly purified (R)-3'-hydroxybutyl (R)-3'-hydroxybutyrate and conducting EEG tests to measure brain activity. According to yet another aspect, a method for analyzing the purity of a pharmaceutical product includes performing stereoisomer analysis to identify and quantify impurities.

According to another aspect, a method for treating metabolic disorders in a subject includes administering a combination of highly purified (R)-3'-hydroxybutyl (R)-3'-hydroxybutyrate and an anti-diabetic drug to the subject.

According to yet another aspect, a method for enhancing mitochondrial function in a subject includes administering a composition containing a purified R-form enantiomer of a ketone ester and measuring mitochondrial biogenesis markers.

According to yet another aspect, a method for treating cardiovascular conditions includes administering highly purified (R)-3'-hydroxybutyl (R)-3'-hydroxybutyrate to a subject. In some of these examples, the method may include monitoring cardiovascular markers. In some examples, the highly purified (R)-3'-hydroxybutyl (R)-3'-hydroxybutyrate composition may include more than 90% composition of the highly purified (R)-3'-hydroxybutyl (R)-3'-hydroxybutyrate enantiomer. In some examples, the highly purified (R)-3'-hydroxybutyl (R)-3'-hydroxybutyrate composition may include more than 99% composition of the highly purified (R)-3'-hydroxybutyl (R)-3'-hydroxybutyrate.

Methods of manufacturing highly pure compositions of (R)-3'-hydroxybutyl (R)-3'-hydroxybutyrate may include various steps. In an example of a transesterification of enantiopure starting materials the following steps may be included. In one example, feeds may be charged to a reactor including a roughly 1:1 molar charge of (R)-1,3-butanediol and the ethyl (R)-3-hydroxybutyrate along with an immobilized lipase. The enzymatic transesterification may be conducted under reduced pressure with continuous ethanol removal, the solids may be removed by filtration, and the filtrate may be subjected to reduced-pressure distillation to remove ethanol, solvent, and unreacted ester. The concentrated product fraction may then be finished by one or more passes of wiped-film evaporation to obtain the highly purified mono-ester (R)-3'-hydroxybutyl (R)-3'-hydroxybutyrate. Subsequently, the product may be transferred to a hold tank. In some examples, an optional chiral/analytical HPLC operation may be interposed for quality confirmation and, where desired, a small-scale polish.

DETAILED DESCRIPTION

Figure 1A:
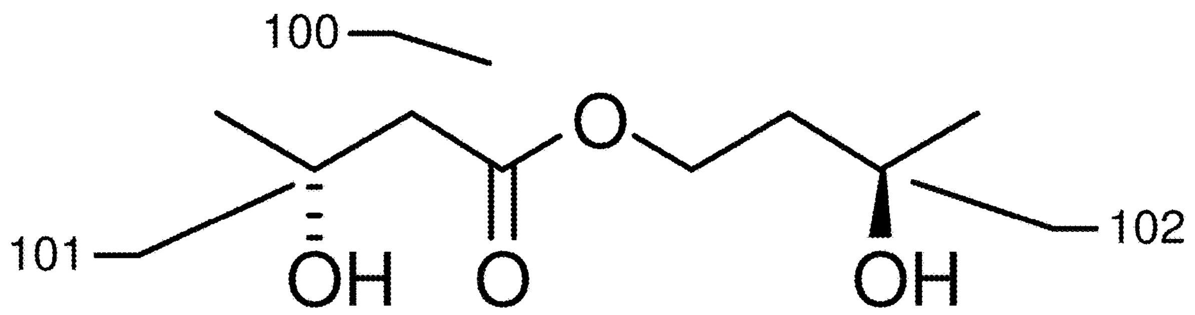
FIGS. 1A-1J.—illustrate the various enantiomers of 3-hydroxybutyrate, 1,3-butanediol, and the enantiomers/stereoisomers of 3'-hydroxybutyl-3'-hydroxybutyrate.
Figure 1B:
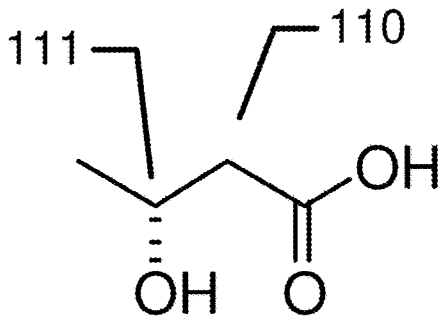
Figure 1C:
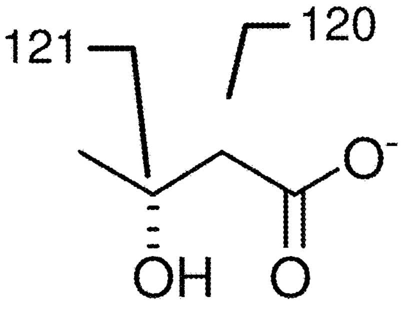
Figure 1D:
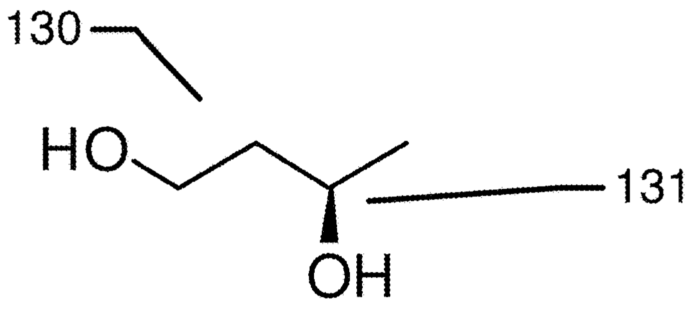
Figure 1E:
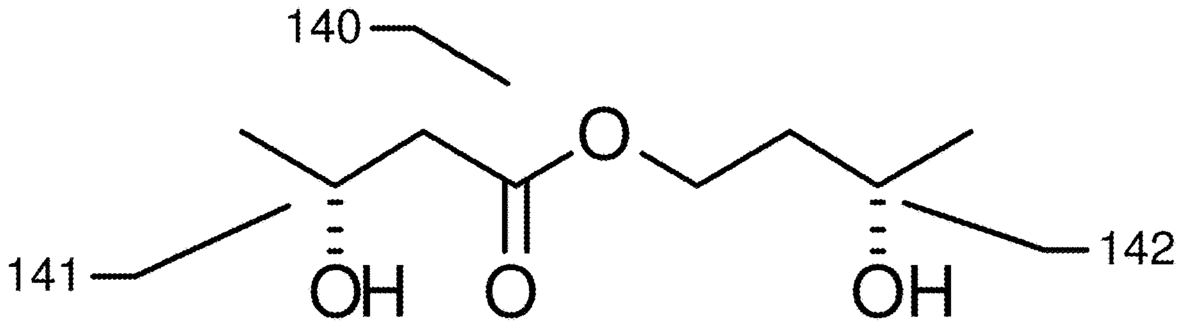
Figure 1F:
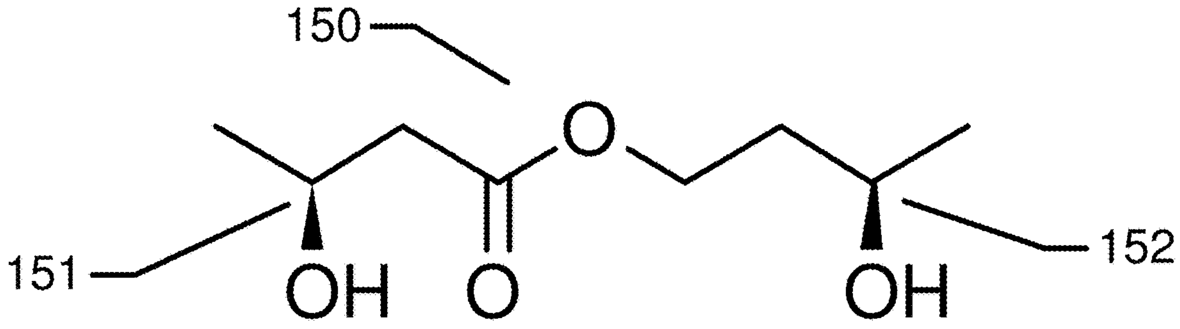
Figure 1G:
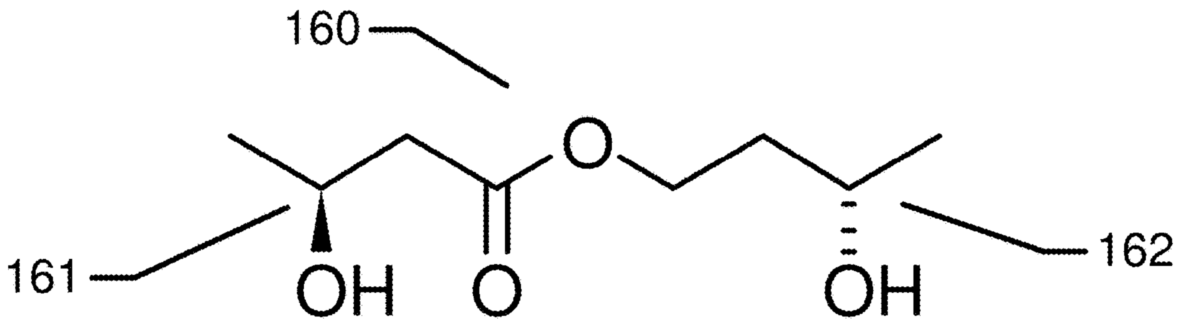
Figure 1H:
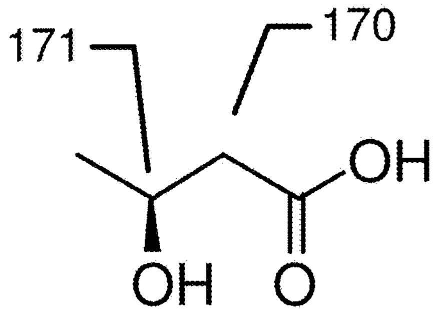
Figure 1I:
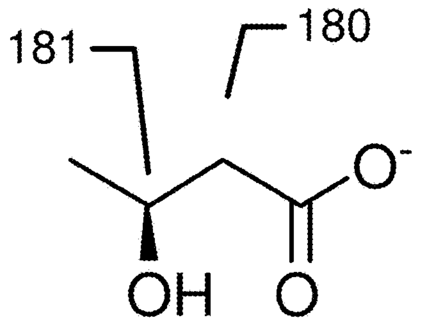
Figure 1J:
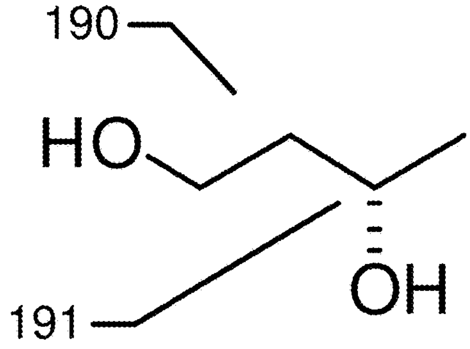
Figure 1K:
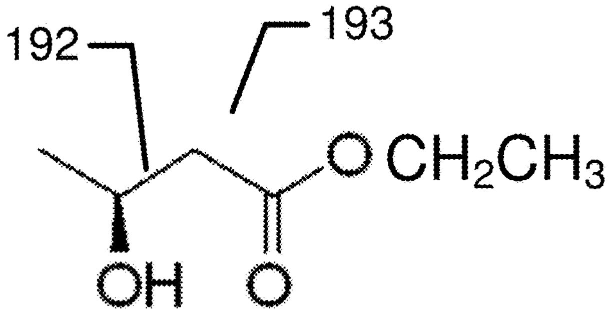
FIG. 1K—illustrates an exemplary ester form of 3-hydroxybutyrate which may be used in various production processes.

According to the present disclosure, highly purified (R)-3'-hydroxybutyl (R)-3'-hydroxybutyrate compositions are described. The metabolism of ingested highly purified (R)-3'-hydroxybutyl (R)-3'-hydroxybutyrate results in the chemical moiety variously termed D-β-hydroxybutyrate, (R)-beta-hydroxybutyrate (BHB) and (R)-3-hydroxybutyric acid, Accordingly, BHB may be provided in a highly pure form from highly purified (R)-3'-hydroxybutyl (R)-3'-hydroxybutyrate. This BHB result may be essentially bioidentical to BHB synthesized in the liver through the metabolism of fatty acids, β-hydroxy β-methylbutyrate, and ketogenic amino acids. In humans the conversion process may include the conversion of these compounds into acetoacetate, a ketone body produced during fasting. The enzyme β-hydroxybutyrate dehydrogenase may catalyze the conversion of acetoacetate into D-β-hydroxybutyrate, which plays an important role in energy metabolism during periods of low carbohydrate availability.

Additionally, a form of D-β-hydroxybutyrate is provided through an alternative metabolic pathway that does not involve acetoacetate. In this pathway, butyrate may be metabolized into butyryl-CoA, and converted into crotonyl-CoA, followed by β-hydroxybutyryl-CoA, poly-β-hydroxybutyrate, and finally D-β-(D-β-hydroxybutyryloxy)-butyrate. The enzyme hydroxybutyrate-dimer hydrolase catalyzes the final step, converting D-β-(D-β-hydroxybutyryloxy)-butyrate into D-β-hydroxybutyrate.

The BHB provided through metabolism of highly purified (R)-3'-hydroxybutyl (R)-3'-hydroxybutyrate is essentially bioidentical with a concentration of BHB in human blood plasma that increases during ketosis, a metabolic state where the body shifts to utilizing fat as its primary energy source due to low glucose levels. The present disclosure provides for an elevation in BHB via an alternative source than its natural formation. According to the present disclosure, BHB is metabolized from highly purified (R)-3'-hydroxybutyl (R)-3'-hydroxybutyrate and may be provided in a pure form as an alternative energy source for the brain and skeletal muscles, particularly when glucose availability is limited.

According to the present disclosure, highly purified (R)-3'-hydroxybutyl (R)-3'-hydroxybutyrate is produced and formulated in various forms for ingestion or injection into a user. The physiological effects of highly purified (R)-3'-hydroxybutyl (R)-3'-hydroxybutyrate ingestion include reduced appetite, increased endurance, and improved mental clarity, though responses may vary based on individual factors. Ingested highly purified (R)-3'-hydroxybutyl (R)-3'-hydroxybutyrate supplements may be rapidly absorbed into the bloodstream, crossing the blood-brain barrier to sustain cognitive function and promote energy efficiency by shifting the body's fuel use from glucose to ketones and fatty acids.

When highly purified (R)-3'-hydroxybutyl (R)-3'-hydroxybutyrate BHB is ingested, it may be processed in the user's gastrointestinal (GI) tract to form both BHB and 1,3-butanediol. These species may be rapidly absorbed into the bloodstream, where the BHB may act as an alternative to glucose for energy and/or produce various therapeutic effects as mentioned herein. In an alternative mechanism, (R)-1,3 Butanediol may course through the blood system of the user and reach the liver where it may subsequently be converted to BHB, forming a longer term presentation of BHB into the bloodstream following ingestion of highly purified (R)-3'-hydroxybutyl (R)-3'-hydroxybutyrate.

Once in the bloodstream, BHB crosses the blood-brain barrier, providing the brain with a stable energy source, which is especially important when carbohydrate intake is low. This ensures the maintenance of cognitive function during periods of reduced glucose availability. The presence of BHB in the blood promotes a state of ketosis, where the body shifts from using glucose as its primary fuel to relying on ketones and fatty acids, optimizing energy utilization.

BHB may also play a role in regulating various metabolic signaling pathways. It has been shown that BHB may inhibit histone deacetylases (HDACs), which may modulate gene expression and potentially provide anti-inflammatory and antioxidant benefits. Additionally, BHB may enhance mitochondrial efficiency and promote the production of proteins associated with stress resistance, longevity, and overall metabolic health.

The physiological effects of (R)-3'-hydroxybutyl (R)-3'-hydroxybutyrate ingestion may include reduced appetite, increased endurance, and improved mental clarity. However, individual responses to (R)-3'-hydroxybutyl (R)-3'-hydroxybutyrate supplementation may vary depending on factors such as diet, physical activity, and metabolic rate.

Ingesting 3-hydroxybutyl-3-hydroxybutyrate, particularly through racemic exogenous supplements, may have several side effects, although most are generally mild. The side effects may vary depending on the individual's health status, dosage, and frequency of consumption. In some examples, formulations with highly enantiomerically pure (R)-3'-hydroxybutyl (R)-3'-hydroxybutyrate may minimize occurrence with side effects. In some other examples, mixtures of highly enantiomerically pure (R)-3'-hydroxybutyl (R)-3'-hydroxybutyrate and other compounds which alleviate the side effects when they occur may be formulated. Side effects may include gastrointestinal issues including nausea, diarrhea and stomach discomfort, electrolyte imbalance and possible kidney stress, hypoglycemia, bad breath, and elevated heart rates. In some examples, particularly with racemic mixtures of 3-hydroxybutyl-3-hydroxybutyrate, unpleasant taste may be a side effect. In some examples, forming combinatorial products of (R)-3'-hydroxybutyl (R)-3'-hydroxybutyrate with other materials may ameliorate these side effects.

Production of Highly Purified (R)-3'-Hydroxybutyl (R)-3'-Hydroxybutyrate

Figure 2:
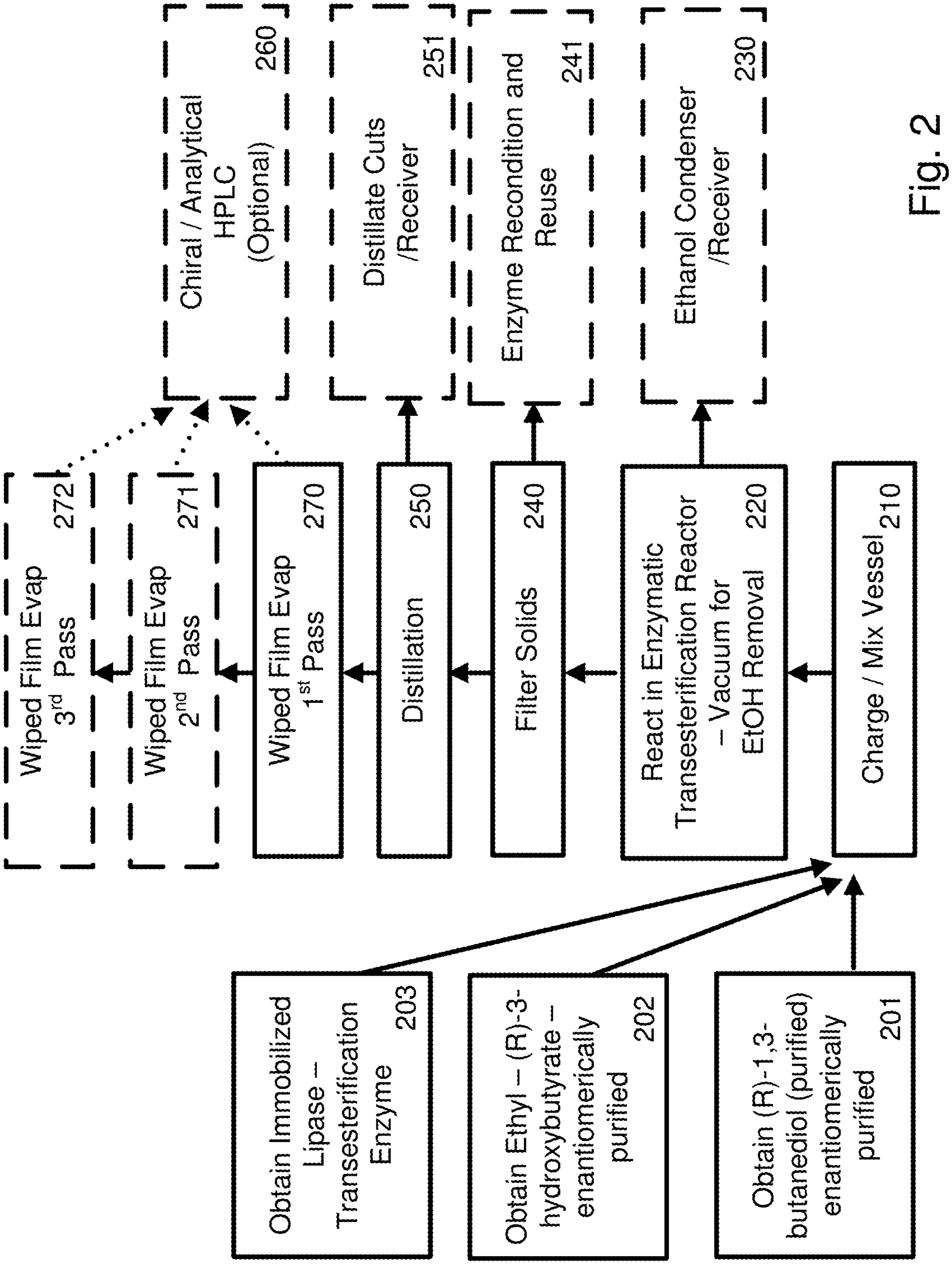
FIG. 2—is a schematic illustration of an exemplary process in accordance with the present disclosure

In some examples, a method for manufacturing enantiomerically pure (R)-3'-hydroxybutyl (R)-3'-hydroxybutyrate monoester comprises an enzymatic transesterification reaction using enantiomerically pure starting materials. Referring to FIG. 2, the process begins by obtaining purified (R)-1,3-butanediol (201) and purified ethyl (R)-3-hydroxybutyrate (202), as well as an immobilized transesterification enzyme (203). The reactants are charged to a mix vessel (210), which is equipped for temperature and pressure control and contains the immobilized enzyme (203). The molar ratio of (R)-1,3-butanediol to ethyl (R)-3-hydroxybutyrate is typically about 1:1, but may be adjusted to a slight excess of (R)-1,3-butanediol (e.g., 1.05-1.20:1) to suppress diester formation. The enzyme loading is generally in the range of 1-25 wt % relative to the total reaction mass. The reaction may be conducted in a hydrophobic organic solvent, such as heptane, toluene, methyl tert-butyl ether, or tert-amyl alcohol, which serves to modulate water activity and enhance selectivity. The mixture is incubated at a temperature of about 25° C. to 50° C., under reduced or ambient pressure (0-759 mm Hg), for a period sufficient to achieve the desired conversion, as monitored by gas chromatography (GC) and/or mass spectrometry (MS). Continuous removal of the ethanol byproduct via a vacuum takeoff and condenser (230) is preferred to drive the equilibrium toward monoester formation. Molecular sieves or other water-scavenging agents may be included to maintain low water activity and preserve stereochemical integrity.

Upon completion of the reaction (220), the mixture is subjected to a workup procedure. This may include the addition of a suitable solvent, such as heptane or ethyl acetate, followed by filtration to remove the immobilized enzyme and any water-scavenging solids (240). The recovered solids may be washed with a non-denaturing solvent and retained for reuse (241). The filtrate is then concentrated by distillation under reduced pressure (250) to remove ethanol, solvent, and unreacted starting materials. The resulting intermediate is further purified by volatility-based finishing techniques, such as wiped-film evaporation (WFE) (270), to afford a highly pure (R)-3'-hydroxybutyl (R)-3'-hydroxybutyrate monoester. WFE parameters, including temperature, pressure, and residence time, are optimized to minimize thermal degradation and racemization while maximizing product recovery and purity. In some embodiments, a second optional WFE pass (271) may be operated at lower absolute pressure and a jacket temperature selected to collect the monoester as the main product cut; and, if necessary, a third pass may be used to route higher-boiling materials, including diester and polycondensed species, to a tails stream (272) for disposition or recycle conditioning.

The immobilized enzyme used in the reaction may be selected from *Candida antarctica* lipase B, *Pseudomonas* (*Burkholderia*) *cepacia* lipase, *Thermomyces lanuginosus* lipase, or *Candida rugosa* lipase, and is typically immobilized on a support such as acrylic resin, silica, or other inert carriers. Immobilization facilitates enzyme recovery and reuse, improving process economics and sustainability. The enzyme may be washed with a non-denaturing solvent and dried under nitrogen between cycles to restore activity. In some embodiments, the enzyme is reused for multiple reaction cycles without significant loss of activity or selectivity.

It may be noted that a variety of enzymatic substrates may be used to catalyze the formation of the desired ester products as described herein. For example, esterification enzymes commonly employed in aqueous reaction chemistries may be utilized. In some embodiments, an enzyme not typically associated with esterification or transesterification may also be used, provided it exhibits catalytic activity toward forming the desired ester end products, particularly where such an enzyme preserves the enantiomeric purity of the products. Furthermore, the enzymes described herein may be employed in either free form or immobilized form, with the free form representing one non-limiting example.

In some additional examples, a variety of non-enzymatic reagents may also be employed to catalyze the formation of the desired ester products as described herein. For example, selective primary esterification may be achieved under controlled conditions using additives such as phosphines, Oxyma derivatives, or Lewis acids including, in a non-limiting perspective, $TiCl_4$, $HfCl_4$, or other suitable Lewis acids. These additives may preferentially esterify less sterically hindered primary alcohols over secondary or tertiary alcohols. In certain embodiments, water removal techniques such as with the use of a Dean-Stark trap in a non-limiting perspective, or the use of mild, aqueous conditions with specific coupling reagents may further enhance results.

The reaction vessel (210) may be equipped for precise control of temperature and pressure, and may include a vacuum takeoff and condenser (230) for continuous ethanol removal. The use of hydrophobic solvents not only modulates water activity but also enhances mass transfer and selectivity for monoester formation. The process may be conducted in batch or continuous flow mode, with continuous flow reactors offering advantages in scalability, process control, and product consistency.

Conversion and selectivity are monitored throughout the process using GC/MS, which may include derivatization of β-hydroxy functionalities when appropriate. Overall assay and impurity profiles are assessed by HPLC, and chiral HPLC is employed to verify enantiomeric excess at each stereocenter. In some embodiments, an intermediate HPLC operation (260) may be included for small-scale or high-purity production, while the principal separations are performed by distillation (250) and wiped-film evaporation (270).

Following the attainment of the desired conversion, the reaction mass is cooled and filtered to remove the immobilized enzyme and any water-scavenging solids (240). The recovered solids may be washed and retained for reuse (241). The filtrate may be subjected to reduced-pressure distillation (250) to remove ethanol, optional solvent, and unreacted ethyl (R)-3-hydroxybutyrate, which may be collected in designated cuts (251) for recycling. Residual (R)-1,3-butanediol may be recovered as a higher-boiling cut and recycled. A dedicated solvent still may be operated to return on-spec solvent to a recycle tank, further minimizing waste.

Further purification may be achieved by wiped-film evaporation (WFE) (270). The concentrated syrup is processed through one or more WFE passes: a first pass to degas the feed and remove residual light ends; a second pass (271) at lower absolute pressure and optimized jacket temperature to collect the monoester as the main product cut; and, if necessary, a third pass to route higher-boiling materials, including diester and polycondensed species, to a tails stream (272) for disposition or recycle conditioning. WFE parameters are tuned to preserve enantiomeric integrity while maximizing separation efficiency.

The immobilized enzyme is separated from the product stream by filtration (240), optionally followed by solvent rinsing and nitrogen drying to restore activity, and may be reused across multiple cycles (241). In embodiments employing a soluble enzyme, a phase-partitioning system or membrane-based ultrafiltration may be used to retain the enzyme while allowing the organic product to pass, after which the enzyme phase may be replenished and recycled. Solvent is recovered by the distillation processing (250) and returned to service via a solvent recycle loop, supporting process sustainability.

Process parameters are selected to maintain low water activity during transesterification, keep ethanol fugacity low to drive equilibrium, and limit residence time at elevated temperature during volatility-based separations. Assay and enantiomeric purity are verified by HPLC and chiral HPLC at release, while routine in-process control relies on GC/MS and non-chiral HPLC. The approach is configured to minimize racemization by avoiding strong acid or base and by employing short thermal exposures within the WFE unit.

The described process enables the scalable, reproducible, and efficient production of enantiomerically pure (R)-3'-hydroxybutyl (R)-3'-hydroxybutyrate monoester, suitable for pharmaceutical and biomedical applications. The process is adaptable to both laboratory and industrial scales, and supports high product purity, yield, and sustainability through recycling of solvents and enzymes, and minimization of waste and byproducts.

In some examples of the present invention, a method for manufacturing purified (R)-3'-hydroxybutyl (R)-3'-hydroxybutyrate involves using a specific enzyme that selectively targets and removes the undesired S-form enantiomer from the starting materials. This enzyme may be derived from a microbial source known for enantioselective properties, ensuring high specificity and efficiency in the purification process. In another example, the method may utilize a combination of enzymatic and chromatographic techniques, where the initial enzymatic step may reduce the S-form enantiomer concentration of starting materials, followed by high-performance liquid chromatography (HPLC) to achieve further purification and ensure the starting materials are pure. In some examples an additional HPLC step may be utilized to ensure the final product meets the desired purity standards.

In some additional examples of the present invention, a method may involve the use of a continuous flow reactor system, where the starting materials may be continuously fed into a reactor containing immobilized enzymes, allowing for a scalable and efficient purification process. This system may be optimized for various flow rates and reaction times to maximize yield and purity. Furthermore, an alternative example might employ a batch processing approach, where the starting materials may be mixed with the enzyme in a controlled environment. In some examples, the reaction may proceed to completion before the product is isolated and purified. This batch method may be particularly useful for small-scale production or for producing high-purity samples for research purposes. Each of these examples may demonstrate that the (R)-3'-hydroxybutyl (R)-3'-hydroxybutyrate may be produced efficiently and with high purity.

Highly Purified (R)-3'-Hydroxybutyl (R)-3'-Hydroxybutyrate and Purity Analysis In some examples of the present invention, a method for analyzing the purity of a (R)-3'-hydroxybutyl (R)-3'-hydroxybutyrate related composition may involve performing stereoisomer analysis using high-performance liquid chromatography (HPLC) equipped with a chiral column. This setup may allow for the separation and quantification of different enantiomers and more generally stereoisomers present in the sample, ensuring precise identification and measurement of impurities or to the control of different mixtures between stereoisomers, although refinements may be needed in some examples for the complexity of esters with dual chiral centers. In other examples, a high degree of purity of (R)-3'-hydroxybutyl (R)-3'-hydroxybutyrate samples may be controlled with the method.

In some embodiments, chiral gas chromatography-mass spectrometry (GC-MS) is employed to analyze the stereoisomeric composition, providing high sensitivity and specificity in detecting even trace amounts of impurities.

Additionally, some embodiments utilize nuclear magnetic resonance (NMR) spectroscopy to determine the stereochemical configuration and purity of the product, offering detailed structural information.

For a more automated and high-throughput approach, an example might incorporate an automated liquid handling system coupled with HPLC or GC-MS, enabling rapid and consistent analysis of multiple samples. Furthermore, an example may involve the use of capillary electrophoresis (CE) with a chiral selector to achieve high-resolution separation of enantiomers, which may be particularly useful for complex mixtures. Each of these examples ensures that the method remains adaptable and effective across various analytical techniques, providing robust and reliable purity analysis of pharmaceutical products.

Highly Purified (R)-3'-Hydroxybutyl (R)-3'-Hydroxybutyrate and Inflammation

Chronic inflammation and metabolic disorders present significant challenges in modern healthcare. These conditions often lead to a cascade of adverse health effects, including cardiovascular diseases, neurodegenerative disorders, and impaired cognitive function. Traditional treatments for these conditions typically involve anti-inflammatory drugs, lifestyle modifications, and various pharmacological interventions aimed at managing symptoms rather than addressing underlying causes. Despite these efforts, there remains a substantial need for more effective and targeted therapies that may mitigate inflammation and improve metabolic health without causing significant side effects.

The disclosed method may address chronic inflammation and metabolic disorders through the administration of highly purified forms of (R)-3'-hydroxybutyl (R)-3'-hydroxybutyrate or mixtures made with highly purified (R)-3'-hydroxybutyl (R)-3'-hydroxybutyrate. In some examples, administration of highly purified (R)-3'-hydroxybutyl (R)-3'-hydroxybutyrate containing therapeutics may leverage properties of BHB to inhibit NLRP3 inflammasome activation, reduce pro-inflammatory cytokines, and enhance mitochondrial function. By targeting multiple pathways involved in inflammation and metabolism, the method may offer a comprehensive solution that addresses the root causes of these conditions.

In some examples, a composition containing highly purified (R)-3'-hydroxybutyl (R)-3'-hydroxybutyrate may be administered to a subject to reduce inflammation, with the composition being delivered orally in the form of a liquid solution. The subject's inflammatory markers in the blood may be monitored using standard blood tests, such as ELISA (enzyme-linked immunosorbent assay) to measure levels of cytokines like IL-6 and TNF-alpha.

In another example a highly purified (R)-3'-hydroxybutyl (R)-3'-hydroxybutyrate composition may be encapsulated in a slow-release capsule to provide a sustained release of the active ingredient over time, ensuring prolonged anti-inflammatory effects. The monitoring of inflammatory markers may be enhanced by using wearable biosensors that continuously measure biomarkers in sweat, providing real-time data on the subject's inflammatory status. In a further example, compositions containing highly enantiomerically purified (R)-3'-hydroxybutyl (R)-3'-hydroxybutyrate may be combined with an anti-inflammatory drug, such as ibuprofen, to provide a synergistic effect in reducing inflammation. The subject's response to the treatment may be monitored through blood tests and imaging techniques to assess inflammation in specific tissues.

In some examples, the method for reducing inflammation in a subject may involve administering a ketone ester composition that includes highly enantiomerically purified (R)-3'-hydroxybutyl (R)-3'-hydroxybutyrate. This composition may be delivered orally in the form of a liquid solution, a gel, or a solid such as a tablet or capsule. The administration may be performed in a single dose or multiple doses over a specified period, depending on the severity of the inflammation and the subject's response to the treatment. The highly purified (R)-3'-hydroxybutyl (R)-3'-hydroxybutyrate containing composition may be combined with other anti-inflammatory agents, such as omega-3 fatty acids or curcumin, to enhance their anti-inflammatory effects.

There may be numerous ways that the highly purified (R)-3'-hydroxybutyl (R)-3'-hydroxybutyrate compositions may elicit a medically effective response through the metabolically produced BHB. In a first example, BHB may act to inhibit NLRP3 inflammasome production or activation. In some understandings, the NLRP3 inflammasome may function as an intracellular sensor that, when activated by a variety of pro-inflammatory stimuli, may trigger secretion of pro-inflammatory cytokines. In some examples, BHB may directly inhibit activation of the NLRP3 inflammasome, thereby preventing secretion of pro-inflammatory mediators, including Interleukins such as IL-1β and IL-18. In some other examples, BHB may also act indirectly to suppress NLRP3 activation by inhibiting K+ efflux from cells. In this way, this may inhibit an upstream signal for NLRP3 inflammasome activation.

There may be numerous disease states where such inhibition of NLRP3 inflammasome may be of clinical relevance. These disease states may include Type 2 diabetes mellitus (T2D), Rheumatoid arthritis (RA), Atherosclerosis, Alzheimer's disease (AD), Psoriatic arthritis, Ankylosing spondylitis, Gout, Myocardial infarction (MI), Stroke, Septic shock syndrome, and Acute Respiratory Distress Syndrome (ARDS) as a non-limiting set of examples. There may also be more rarely occurring disease states where such means of inhibition of inflammation provided by highly purified (R)-3'-hydroxybutyl (R)-3'-hydroxybutyrate containing compositions may be important and helpful including Cryopyrin-associated periodic syndrome (CAPS), Familial Mediterranean fever (FMF), Hemophagocytic lymphohistiocytosis (HLH), Hyperimmunoglobulinemia D and periodic fever syndrome (HIDS)/Mevalonate kinase deficiency (MKD), Tumor Necrosis Factor Receptor-1-associated syndrome (TRAPS), Pyogenic Arthritis, Pyoderma Gangrenosum, and Acne syndrome (PAPA) as a further non-limiting set of examples.

In some examples, highly purified (R)-3'-hydroxybutyl (R)-3'-hydroxybutyrate containing compositions may be effective through the action of BHB to inhibit NF-kB via GPR109A. In some examples, this may subsequently reduce IL-6. BHB may act as an activator of the GPR109A receptor, which is expressed in various cell types, including those involved in immune responses. Activation of the GPR109A receptor by R-BHB may support anti-inflammatory effects primarily through the suppression of NF-kappaB, a transcription factor regulating the expression of numerous pro-inflammatory cytokines.

In another simultaneous example, the promoter region of the IL-6 gene contains a binding site for NF-κB, which may be essential for IL-6 gene activation. This NF-kB may itself be sensitive to oxidative stress. The role of BHB may be to provide antioxidative effects on multiple levels such as regulation from decreasing reactive oxygen species by preventing reverse transport chain or increasing the expression of endogenous antioxidants such as SOD2 or MT2. The binding of NF-κB to this site is necessary for the inducibility of the IL-6 promoter. By reducing NF-kappaB activity, BHB potentially decreases pro-inflammatory cytokine production. Additionally, BHB may also exert anti-inflammatory effects through other pathways, such as the inhibition of histone deacetylases (HDACs), which may indirectly affect NF-kappaB activity.

There may be numerous disease states where elevated levels of IL-6 are found and where modulation by treatment with highly purified (R)-3'-hydroxybutyl (R)-3'-hydroxybutyrate containing compositions to reduce levels of IL-6 may result in effective treatments. These disease states may include Type 2 Diabetes Mellitus, Cardiovascular Diseases (including myocardial infarction and atherosclerosis), Obesity, Asthma, Chronic Obstructive Pulmonary Disease (COPD), Rheumatoid Arthritis (RA), Alzheimer's Disease (AD), Inflammatory Bowel Disease (IBD) (including Crohn's Disease and Ulcerative Colitis) as a set of non-limiting examples. There may also be relevance to more rarely occurring disease states as well including Systemic Lupus Erythematosus (SLE), Severe Sepsis and Septic Shock, Multiple Sclerosis, HIV Infection, Systemic Juvenile Idiopathic Arthritis (sJIA), Castleman Disease (CD), and Chronic inflammatory pulmonary diseases (such as interstitial lung disease) as a set of non-limiting examples.

In some examples, BHB may inhibit TNF-alpha via NF-kB inhibition. Similarly to IL-6, TNF-alpha may also be activated by NF-kB so BHB may inhibit it via the GPR109A activation. Moreover, BHB may also activate Nrf2 which was shown to inhibit supress TNF-alpha production. Furthermore, the antioxidative effects may also lower TNF-alpha activity. There may be various disease states where lowered TNF-alpha levels may be of clinical relevance. In some examples, in the elderly, higher TNF-alpha levels were associated with mortality in men but not women. In some other non-limiting examples, diseases associated with high TNF-alpha levels may include Rheumatoid Arthritis, Psoriatic Arthritis, Juvenile Idiopathic Arthritis, Ankylosing Spondylitis, Psoriasis, Crohn's Disease, Ulcerative Colitis, COVID-19, Autoinflammatory Syndromes, Septic Shock, Inflammatory Bowel Disease (IBD), Autoimmune Lymphoproliferative Syndrome (ALPS).

In some examples, BHB may cause an adenosine-mediated anti-inflammatory effect. The mechanism involving adenosine may contribute to anti-inflammatory effects of BHB. In some examples, ketone metabolism may lead to an increase in adenosine levels. Adenosine may exert anti-inflammatory effects through its interaction with A1 and A2 receptor subtypes in both peripheral and central tissues. BHB may mitigate HIF-1α-induced inflammation and oxidative stress by activating the adenosine A1 receptor, thus offering a potential therapeutic pathway for managing inflammation.

The most common effects of adenosine receptor anti-inflammatory actions are lower levels of IL-6 and TNF-alpha. However, it may also activate A2A receptors and augment production of IL-10 which is an anti-inflammatory cytokine that blocks the expression of multiple pro-inflammatory cytokines, including IL-1, IL-6 and TNF-alpha and inhibiting the NF-kB pathway. Such action may have clinical relevance for disease states, including in a non-limiting perspective, Inflammatory Bowel Disease, Metabolic Syndrome, T2D, Asthma, Rheumatoid Arthritis, Psoriasis and Systemic Lupus Erythematosus.

In some examples, highly purified (R)-3'-hydroxybutyl (R)-3'-hydroxybutyrate may induce macrophage phenotype switching. The mechanism may induce and influence switching between M1 and M2 macrophages. In some examples, BHB may promote the polarization of macrophages towards the M2 phenotype, which may be associated with anti-inflammatory properties. In some examples, this effect may be mediated via two pathways: HDAC inhibition and GPT109A signalling. In HDAC Inhibition, BHB-mediated inhibition of histone deacetylases (HDACs) may increase expression of anti-inflammatory cytokines like IL-10 and promote the M2 macrophage phenotype. In GPR109A signalling, activation of the hydroxycarboxylic acid receptor 2 (HCAR2 or GPR109A) by BHB may also contribute to M2 polarization by inhibiting the NF-kB pathway and reducing the production of pro-inflammatory cytokines typical of M1 macrophages. These two pathways may, therefore, have clinical relevance to diseases which may be associated when M1 is the dominant macrophage phenotype. These diseases many include, in a non-limiting sense, Atherosclerosis, Obesity, Rheumatoid Arthritis, Tuberculosis, Cancer, Sepsis, Chronic Obstructive Pulmonary Disease (COPD), Systemic Lupus Erythematosus (SLE), Neurodegenerative Diseases (e.g., Alzheimer's disease, Parkinson's disease), and Diabetic Wound Healing.

Highly Purified (R)-3'-Hydroxybutyl (R)-3'-Hydroxybutyrate and Cognitive Function In certain examples, the method for enhancing cognitive function in a subject may involve administering an effective amount of highly purified (R)-3'-hydroxybutyl (R)-3'-hydroxybutyrate through oral ingestion. The highly purified (R)-3'-hydroxybutyl (R)-3'-hydroxybutyrate may be prepared as a liquid solution, gel, or encapsulated in a pill to make consumption easier and improve taste. Depending on the subject's needs and the desired cognitive enhancement, administration may occur in a single dose or multiple doses throughout the day.

Alternatively, highly purified (R)-3'-hydroxybutyl (R)-3'-hydroxybutyrate may be delivered via a transdermal patch, providing a controlled release of the active compound over an extended period, which helps maintain steady BHB levels in the blood. This approach may be especially beneficial for subjects who have difficulty with oral ingestion or need a prolonged cognitive boost.

Additionally, highly purified (R)-3'-hydroxybutyl (R)-3'-hydroxybutyrate may be combined with other cognitive enhancers, such as caffeine or nootropic compounds, to potentially enhance the cognitive benefits. The method may be customized for different populations, including healthy individuals seeking improved mental performance, elderly subjects aiming to preserve cognitive function, and patients with cognitive impairments due to psychiatric conditions or neurodegenerative diseases. Cognitive function may be monitored using standardized cognitive tests, EEG measurements, or other neurophysiological assessments to evaluate the treatment's effectiveness.

In some examples, the method for improving cognitive performance in subjects with psychiatric conditions may involve administering highly purified (R)-3'-hydroxybutyl (R)-3'-hydroxybutyrate in a liquid form, which may be ingested orally. The highly purified (R)-3'-hydroxybutyl (R)-3'-hydroxybutyrate composition may be formulated to include additional ingredients such as flavor enhancers or stabilizers to improve palatability and shelf-life. The administration may be done daily over a specified period, such as four weeks, to observe significant cognitive improvements. EEG tests are conducted at baseline and at regular intervals during the treatment period to measure changes in brain activity, focusing on specific cognitive domains like attention, memory, and executive function. In another example, the highly purified (R)-3'-hydroxybutyl (R)-3'-hydroxybutyrate comprising composition may be delivered in a capsule or tablet form, providing an alternative for subjects who prefer not to consume liquid supplements. The dosage and frequency of administration may be adjusted based on the severity of the psychiatric condition and the subject's response to the treatment. Additionally, the EEG tests may be complemented with other neuroimaging techniques such as fMRI to provide a more comprehensive assessment of brain function. In a further example, the method may include a combination of highly purified (R)-3'-hydroxybutyl (R)-3'-hydroxybutyrate administration with cognitive behavioral therapy (CBT) sessions, aiming to enhance the overall therapeutic effect. The EEG tests in this case may not only measure brain activity but also track changes in neural connectivity patterns associated with cognitive and emotional regulation. This multi-faceted approach may allow for a more personalized treatment plan, potentially leading to better outcomes for subjects with psychiatric conditions.

In some examples, the method for improving cognitive function in elderly subjects may involve administering a highly purified (R)-3'-hydroxybutyl (R)-3'-hydroxybutyrate composition in a liquid form, such as a drink or a solution, which may be easily ingested and absorbed by the body. The composition may include additional ingredients like electrolytes or flavoring agents to enhance palatability and ensure better compliance among elderly subjects. In another example, the highly purified (R)-3'-hydroxybutyl (R)-3'-hydroxybutyrate composition may be administered in a solid form, such as capsules or tablets, which may be preferred for ease of storage and precise dosing.

Cognitive tests conducted to measure improvements may vary, including standardized tests for memory recall, executive function, and attention span, tailored to the cognitive abilities and limitations of elderly subjects. Additionally, methods of the present invention may incorporate the use of wearable devices to monitor physiological parameters such as heart rate variability and sleep patterns, providing a comprehensive assessment of the cognitive and overall health benefits of the highly purified (R)-3'-hydroxybutyl (R)-3'-hydroxybutyrate composition. In a further example, the administration of the highly purified (R)-3'-hydroxybutyl (R)-3'-hydroxybutyrate composition may be combined with a structured cognitive training program, where subjects engage in specific mental exercises designed to enhance cognitive function, thereby potentially amplifying the benefits of the highly purified (R)-3'-hydroxybutyl (R)-3'-hydroxybutyrate. The frequency and duration of administration may also vary, with some protocols involving daily doses while others might use intermittent dosing schedules to optimize cognitive outcomes.

In some examples of the present invention, the method for enhancing cognitive function in subjects with schizophrenia may involve administering a highly purified (R)-3'-hydroxybutyl (R)-3'-hydroxybutyrate composition in a controlled clinical setting, where the dosage and frequency of administration are tailored to the individual needs of the patient based on their medical history and current health status. The highly purified (R)-3'-hydroxybutyl (R)-3'-hydroxybutyrate composition may be delivered in various forms, such as oral capsules, liquid solutions, or even intravenous infusions, depending on the patient's ability to ingest and metabolize the compound effectively. Cognitive tests, such as the Wisconsin Card Sorting Test (WCST) and the Continuous Performance Test (CPT), may be conducted to measure improvements in executive function, attention, and working memory. Additionally, EEG tests may be performed to monitor brain activity, focusing on specific biomarkers associated with cognitive function in schizophrenia, such as gamma oscillations and P300 waveforms. In another example, the method may include a combination therapy approach, where the highly purified (R)-3'-hydroxybutyl (R)-3'-hydroxybutyrate composition may be administered alongside standard antipsychotic medications to evaluate potential synergistic effects on cognitive enhancement. This combination therapy may be monitored through regular blood tests to measure ketone levels and ensure there are no adverse interactions between the ketone ester and the antipsychotic drugs. Furthermore, the method may be adapted to include lifestyle interventions, such as dietary modifications and exercise regimens, to support overall metabolic health and enhance the efficacy of the highly purified (R)-3'-hydroxybutyl (R)-3'-hydroxybutyrate composition. In a third example, the method may incorporate the use of wearable technology to continuously monitor physiological parameters, such as heart rate variability and sleep patterns, providing real-time data to adjust the treatment protocol dynamically. This personalized approach may ensure that the cognitive enhancement strategy is optimized for each individual, considering their physiological responses and lifestyle factors.

In some embodiments, methods for improving cognitive function in subjects with bipolar disorder involve administering a highly purified (R)-3'-hydroxybutyl (R)-3'-hydroxybutyrate composition in a liquid form, which may be ingested orally. The highly purified (R)-3'-hydroxybutyl (R)-3'-hydroxybutyrate composition may be formulated to include additional ingredients such as electrolytes and flavoring agents to enhance palatability and absorption. The administration may be done daily over a period of several weeks, with cognitive tests conducted at regular intervals to measure improvements in various domains such as memory, attention, and executive function. In another example, the highly purified (R)-3'-hydroxybutyl (R)-3'-hydroxybutyrate composition may be delivered via a slow-release capsule, allowing for a more controlled and sustained release of the active compound. This method may be particularly beneficial for subjects who have difficulty with frequent dosing. Additionally, the cognitive tests may be complemented with EEG tests to monitor brain activity and assess the impact of the ketone ester on neural function. In a further example, the highly purified (R)-3'-hydroxybutyl (R)-3'-hydroxybutyrate composition may be combined with other therapeutic agents, such as mood stabilizers or antipsychotic medications, to provide a synergistic effect on cognitive function. This combination therapy may be tailored to the individual needs of the subject, with dosages adjusted based on periodic assessments of cognitive performance and overall health. The method may also include the use of wearable devices to monitor physiological markers such as heart rate variability and sleep patterns, providing a comprehensive approach to evaluating the benefits of the highly purified (R)-3'-hydroxybutyl (R)-3'-hydroxybutyrate composition on cognitive function in subjects with bipolar disorder.

In some examples, the method for enhancing cognitive function in healthy subjects may involve administering a highly purified (R)-3'-hydroxybutyl (R)-3'-hydroxybutyrate composition in a liquid form, such as a drink or a solution, which may be flavored to improve palatability. The composition may include additional ingredients like electrolytes or vitamins to support overall health and enhance the cognitive benefits. In another example, the highly purified (R)-3'-hydroxybutyl (R)-3'-hydroxybutyrate composition is provided in a solid form, such as capsules or tablets, which may be taken orally with water. This form may be preferred for individuals who require precise dosing or have dietary restrictions. Additionally, the method may be adapted to different administration schedules, such as a single daily dose or multiple smaller doses throughout the day, depending on the subject's needs and lifestyle. The cognitive function improvements may be measured using a variety of validated cognitive tests, including those assessing executive function, memory, attention, and reaction times. Furthermore, the method may be tailored to different age groups, with specific formulations and dosages designed for younger adults, middle-aged individuals, and the elderly, ensuring that the cognitive benefits are optimized for each demographic. The highly purified (R)-3'-hydroxybutyl (R)-3'-hydroxybutyrate composition may also be combined with other nootropic agents or cognitive enhancers to create a synergistic effect, potentially leading to greater improvements in cognitive performance. The method may include monitoring biomarkers such as blood ketone levels, metabolic markers, and neuroprotective markers to assess the efficacy and safety of the highly purified (R)-3'-hydroxybutyl (R)-3'-hydroxybutyrate composition over time.

Highly Purified (R)-3'-Hydroxybutyl (R)-3'-Hydroxybutyrate and Neurodevelopmental, Psychiatric and Neurodegenerative Disease In some examples, the method for treating neurodegenerative diseases may involve administering a highly purified (R)-3'-hydroxybutyl (R)-3'-hydroxybutyrate composition formulated to enhance neuroprotective effects. This composition may include highly purified (R)-3'-hydroxybutyl (R)-3'-hydroxybutyrate, which may be metabolized to generate BHB which has been shown to improve mitochondrial function and reduce oxidative stress. The administration may be done orally, through a liquid or capsule form, ensuring ease of use for patients. In another example, the highly purified (R)-3'-hydroxybutyl (R)-3'-hydroxybutyrate composition may be combined with other neuroprotective agents, such as antioxidants or anti-inflammatory compounds, to provide a synergistic effect. This combination may be tailored based on the neurodegenerative condition being treated, such as Alzheimer's disease, Parkinson's disease, or amyotrophic lateral sclerosis (ALS). Additionally, the treatment regimen may involve varying dosages and frequencies of administration, depending on the severity of the disease and the patient's response to the treatment. Monitoring neuroprotective markers in the blood, such as brain-derived neurotrophic factor (BDNF) and inflammatory cytokines, may be a part of the treatment protocol to assess efficacy and make necessary adjustments. Furthermore, the method may be adapted to include non-invasive brain imaging techniques, like functional MRI or PET scans, to observe changes in brain activity and structure over time, providing a comprehensive approach to managing neurodegenerative diseases.

In some examples, the method for treating neurodegenerative diseases may involve administering a highly purified (R)-3'-hydroxybutyl (R)-3'-hydroxybutyrate composition formulated to enhance neuroprotective effects. This composition may include a purified R-form enantiomer of a ketone ester, which has been shown to improve mitochondrial function and reduce oxidative stress. The administration may be done orally, through a liquid or capsule form, ensuring ease of use for patients. In another example, the highly purified (R)-3'-hydroxybutyl (R)-3'-hydroxybutyrate composition may be combined with other neuroprotective agents, such as antioxidants or anti-inflammatory compounds, to provide a synergistic effect. This combination may be tailored based on the neurodegenerative condition being treated, such as Alzheimer's disease, Parkinson's disease, or amyotrophic lateral sclerosis (ALS). Additionally, the treatment regimen may involve varying dosages and frequencies of administration, depending on the severity of the disease and the patient's response to the treatment. Monitoring neuroprotective markers in the blood, such as brain-derived neurotrophic factor (BDNF) and inflammatory cytokines, may be a part of the treatment protocol to assess efficacy and make necessary adjustments. Furthermore, the method may be adapted to include non-invasive brain imaging techniques, like functional MRI or PET scans, to observe changes in brain activity and structure over time, providing a comprehensive approach to managing neurodegenerative diseases.

In some examples, the use of highly purified (R)-3'-hydroxybutyl (R)-3'-hydroxybutyrate in a treatment protocol may involve numerous mechanisms or effects. In a non-limiting example, BHB may serve as an alternative energy source. In another example, BHB may act by reducing oxidative stress in the user. In some non-limiting examples, BHB decreases the production of reactive oxygen species (ROS) by increasing the Q/QH2 ratio in the electron transport chain, which reduces reverse electron transport and consequently the generation of superoxide radicals. Additionally, BHB may enhance the NADP+/NADPH ratio, supporting the synthesis of antioxidants like glutathione, thioredoxins, and vitamins C and E. For these effects there may be numerous disease states of clinical relevance that may be improved including, in a non-limiting perspective, Alzheimer's disease, Parkinson's disease, Huntington's disease, Amyotrophic Lateral Sclerosis (ALS)/Motor Neuron Disease, and Multiple sclerosis. In some other examples, other rarer disease states that may be improved include Friedreich's Ataxia, Creutzfeldt-Jakob Disease, Spinocerebellar Ataxia, Lewy Body Dementia, and Progressive Supranuclear Palsy. Apart from the neurodegenerative diseases, the reduction of oxidative stress in neurons may also be relevant for TBI and metabolic psychiatry (autism, bipolar disease, or schizophrenia). As part of a treatment methodology, there may be numerous biomarkers that may be used for assessment. These biomarkers to assess the anti-oxidative effects may include, Isoprostanes which may be common plasma markers of lipid oxidation, 7,8-dihydro-8-oxo-2'-deoxyguanosine which may be a marker of DNA oxidative damage. Other markers may include Thiobarbituric Acid Reducing Substances (TBARS) or 8-Iso-Prostaglandin-F2$\alpha$ (F2-IsoPs), and Protein carbonyls as non-limiting cases.

In some examples, the use of highly purified (R)-3'-hydroxybutyl (R)-3'-hydroxybutyrate may involve a mechanism wherein generated BHB may induce anti-inflammatory effects. In some examples, BHB may exert anti-inflammatory effects by binding to hydroxycarboxylic acid receptor 2 (HCAR2), which inhibits the nuclear factor-kappa B (NF-$\kappa$B) pathway. This inhibition may reduce the expression of pro-inflammatory cytokines such as TNF-$\alpha$ and IL-1$\beta$, and suppresses inflammasome activation, particularly the NLRP3 inflammasome, thereby reducing neuroinflammation. There may be numerous disease states where such effects of the treatment with highly purified (R)-3'-hydroxybutyl (R)-3'-hydroxybutyrate may have clinical relevance including in a non-limiting perspective: Alzheimer's, Parkinson's, ALS, Huntington's disease, multiple sclerosis, frontotemporal dementia or progressive supranuclear palsy. There may also be links between neuroinflammation and TBI and psychiatric diagnoses such as autism, depression, bipolar disease, or schizophrenia. As part of a treatment protocol there may be measurements of various biomarkers including serum levels of IL-1beta, IL-6, IL-10, TNF-alpha and C-reactive protein (CRP) for example.

In some examples, the use of highly purified (R)-3'-hydroxybutyl (R)-3'-hydroxybutyrate may involve a mechanism wherein BHB may mediate enhancement of mitochondrial function. In some examples, BHB may improve mitochondrial function by increasing the activity of enzymes like Peroxisome Proliferator-Activated Receptor Gamma Coactivator 1-alpha (PGC-1$\alpha$), which may be important for mitochondrial biogenesis. BHB may also stimulate the deacetylation of transcription factors such as Sirtuin 1 (SIRT1), enhancing the expression of antioxidant genes and improving the health of the mitochondrial pool.

In some examples, the use of highly purified (R)-3'-hydroxybutyl (R)-3'-hydroxybutyrate may involve a mechanism wherein BHB may induce autophagy. BHB may stimulate autophagic flux, which may be vital for degrading and recycling damaged cellular components, including defective mitochondria. This process may be regulated through pathways involving SIRT1, AMP-activated protein kinase (AMPK), Unc-51-like kinase 1 (ULK1), and mTORC1. By enhancing autophagy, BHB may help maintain cellular homeostasis and prevents the accumulation of toxic protein aggregates. These improvements may be useful in treatment of disease states such as Alzheimer's amongst others. There may be methods of treatment which may include assessment of biomarkers to regulate the treatment, these biomarkers may include, in a non-limiting perspective, serum level of ATG5 protein or Parkin proteins.

In some examples, the use of highly purified (R)-3'-hydroxybutyl (R)-3'-hydroxybutyrate may involve a mechanism wherein BHB may regulate apoptosis. BHB may modulate apoptotic pathways by inhibiting pro-apoptotic factors like p53 and promoting the expression of anti-apoptotic proteins. This regulation may reduce neuronal apoptosis and may support cell survival under stress conditions. These improvements may be useful in treatment of disease states such as Alzheimer's, Huntington's, Parkinson's, ALS, TBI and stroke amongst others. There may be methods of treatment which may include assessment of biomarkers to regulate the treatment, these biomarkers may include in a non-limiting perspective caspase-3 in cerebrospinal fluid is a marker of neuronal apoptosis after strokes or TBI. For TBI serum levels of S100B and GFAP may be used as biomarkers, in some examples.

Highly Purified (R)-3'-Hydroxybutyl (R)-3'-Hydroxybutyrate and Metabolic Disorders Given its function as an alternative cerebral energy substrate to glucose during restricted dietary access to carbohydrates, R-BHB may be inherently associated with states of low-calorie availability. This may make highly purified (R)-3'-hydroxybutyl (R)-3'-hydroxybutyrate a good candidate as a molecule not only to provide an alternative source of energy but also to elicit various cellular processes which facilitate the adaptation to low-calorie states. In some examples, calorie restriction may alleviate a wide range of non-communicable disease states, it may be expected that compounds which may mimic the adaptations to stresses of low calories may also prevent and treat diseases, BHB generated from highly purified (R)-3'-hydroxybutyl (R)-3'-hydroxybutyrate may therefore be considered to be a calorie restriction mimetic.

The set of adaptations required for the reprogramming of the metabolic profile of cells and organs may be extensive. Similarly, the signaling effects of BHB may also be relatively broad which may make highly purified (R)-3'-hydroxybutyl (R)-3'-hydroxybutyrate well-positioned to act as a multi-target therapeutic.

In some examples, BHB may act to improve metabolic disorders through a mechanism of increasing AMPK activity. In some examples, AMPK may act as a sensor of cellular energy. Once it is activated, AMPK may restore energy balance by promoting energy-generating processes and inhibiting energy-consuming processes. For example, this inhibition may come through increased mitochondrial biogenesis, activated autophagy, inhibition of the mechanistic Target of Rapamycin (mTOR) complex or promotion of uptake of glucose from bloodstream independently of insulin.

For example, a specific type of post-translational modification of histone proteins, which may be referred to as Kbhb, may involve the addition of a BHB group to lysine residues on histone proteins which DNA wraps around. By changing the chromatin structure through the Kbhb mechanism, the accessibility of DNA sequences may change. Accordingly, Kbhb may result in changes to regulation of gene expression. In some studies, the genes affected by Kbhb have been characterized. Downregulated genes were mainly involved in glycolysis and ribosome assembly pathways, while upregulated genes were involved in mitochondrial metabolism.

In some other examples, Kbhb may also occur on lysine residues of nonhistone proteins. In some examples, Kbhb associated proteins may be involved in spliceosome, ribosome, and RNA transport functions. There also may also be a role for Kbhb associated proteins in DNA repair-related pathways, such as nucleotide excision repair, mismatch repair, and base excision repair. In some examples, these Kbhb associated proteins may be highly enriched, with 43, 57, and 39% of proteins in these pathways being beta-hydroxybutyrylated.

In a different set of examples, highly purified (R)-3'-hydroxybutyl (R)-3'-hydroxybutyrate may act to improve metabolic disorders through a mechanism involving generated BHB and histone deacetylase (HDAC) inhibition. HDAC refers to a process which removes acetyl groups from histone proteins. In a similar manner to the process of Kbhb, the inhibition of histone deacetylation may change the structure of the chromatin and, accordingly, may influence gene expression. In some examples, numerous signaling effects of BHB are mediated by HDAC inhibition. In a non-limiting example, the activation of Forkhead Box O3 (FOXO3) transcription factor by BHB may be facilitated by HDAC inhibition.

In a different set of examples, highly purified (R)-3'-hydroxybutyl (R)-3'-hydroxybutyrate may act to BHB to improve metabolic disorders through a mechanism involving regulation of inflammation such as through NOD-like receptor family pyrin domain containing 3 (NLRP3) protein inhibition by BHB. In some examples, NLRP3 may be an inflammasome necessary for the activation of pro-inflammatory cytokine. In similar examples, Nuclear Factor kappa B (NF-kappaB) proteins may be inhibited by BHB. NF-kappaB may control the production of pro-inflammatory cytokines.

In a still further different set of examples, highly purified (R)-3'-hydroxybutyl (R)-3'-hydroxybutyrate may act through generated BHB to improve metabolic disorders through a mechanism involving increased mitochondrial biogenesis. In some examples, R-BHB may upregulate expression of PGC-1alpha. PGC-1alpha may be a master regulator of mitochondrial biogenesis.

In additional examples, highly purified (R)-3'-hydroxybutyl (R)-3'-hydroxybutyrate may act to improve metabolic disorders through generated BHB through a mechanism involving the induction of autophagy. In some examples, BHB treatment may induce autophagic flux, as related to the upregulation of autophagy-related proteins like BECN1 and the downregulation of p62, an autophagy adaptor protein.

In some examples, highly purified (R)-3'-hydroxybutyl (R)-3'-hydroxybutyrate may act through generated BHB to improve metabolic disorders through a mechanism involving enhancement of Brain-Derived Neurotrophic Factor (BDNF) expression. In some examples, R-BHB may increase BDNF expression. The primary function of BDNF may be to support the survival, growth, and maintenance of neurons in the brain and peripheral nervous system.

In some examples, highly purified (R)-3'-hydroxybutyl (R)-3'-hydroxybutyrate may act through generated BHB to improve metabolic disorders through a mechanism involving activation of hydroxycarboxylic acid receptor 2 (HCAR2). This receptor may also be known as PUMA-G and GPR109A, and its activation may inhibit lipolysis in adipocytes, lower plasma FFA and glucose levels in individuals with type 2 diabetes and contribute to neuroprotection in the brain.

In some examples, highly purified (R)-3'-hydroxybutyl (R)-3'-hydroxybutyrate may act through generated BHB to improve metabolic disorders through a mechanism involving promotion of Vascular Endothelial Growth Factor (VEGF) production. VEGF may be a master regulator of vascular growth, and BHB was shown to promote VEGF production. In some of these examples, such an effect may alleviate diabetic aortic endothelial injury as a non-limiting example.

In some examples, highly purified (R)-3'-hydroxybutyl (R)-3'-hydroxybutyrate may act through BHB to improve metabolic disorders through a mechanism involving prevention of DNA damage by the alleviation of oxidative stress. Oxidation of BHB may reduce oxidative stress by replenishing coenzyme Nicotinamide Adenine Dinucleotide Phosphate (NADPH) levels and increasing the Ubiquinone (Q also called CoQ10) to Ubiquinol (QH2—a reduced form of Ubiquinone) ratio. Moreover, BHB may also stimulate the activity of FOXO3a (an isoform of FOX03) via HDAC inhibition and Nrf2 activity which results in the expression of endogenous antioxidants like catalase, Glutamate-Cysteine Ligase (GCL) and Manganese Superoxide Dismutase (mnSOD).

In some examples, highly purified (R)-3'-hydroxybutyl (R)-3'-hydroxybutyrate may act through generated BHB to improve metabolic disorders through a mechanism involving affecting biochemical pathways which regulate cellular senescence. BHB may react to form beta-hydroxybutyrylate lysine residues on various proteins, including the p53 protein. The beta-hydroxybutyrylation may attenuate Tumor Protein 53 (p53) activity and downregulates levels of Tumor Protein 21 (p21). Another study showed that BHB may mitigate senescence in the kidney by decreasing the expression of Tumor Protein 16 (p16) and p21.

In vascular cells, BHB prevented senescence by increasing Lamin B1 via stabilization of Octamer-binding transcription factor 4 (Oct 4 mRNA).

In some examples, the method for treating metabolic disorders in a subject may involve administering a combination of highly purified (R)-3'-hydroxybutyl (R)-3'-hydroxybutyrate and an anti-diabetic drug or R-BHB and an anti-diabetic drug such as metformin, to the subject. In other examples, the combination may be with one or more of the following materials including diuretics and glucagon like protein-1 receptor agonists including but not limited to semaglutide, liraglutide, exenatide, dulaglutide, lixisenatide, albiglutide and efpeglenatide. In some other examples, highly purified (R)-3'-hydroxybutyl (R)-3'-hydroxybutyrate may be combined with dual glucagon like protein-1 receptor agonist and glucose-dependent insulinotropic polypeptide receptor agonist molecules such as tirzepatide.

The highly purified (R)-3'-hydroxybutyl (R)-3'-hydroxybutyrate will generate a purified R-form enantiomer of BHB, which enhances the metabolic benefits by providing a more efficient energy source and reducing oxidative stress. The anti-diabetic drug may be administered in various forms, including oral tablets, capsules, or injectable solutions, depending on the subject's specific needs and medical conditions. In another example, highly purified (R)-3'-hydroxybutyl (R)-3'-hydroxybutyrate may be combined with a different class of anti-diabetic drugs, such as SGLT2 inhibitors including but not limited to Canagliflozin, Dapagliflozin, Empagliflozin, and Ertugliflozin, to further enhance glucose regulation and improve insulin sensitivity.

The administration may be tailored to the subject's daily routine, with highly purified (R)-3'-hydroxybutyl (R)-3'-hydroxybutyrate being taken in the morning to provide sustained energy throughout the day, and the anti-diabetic drug being taken in the evening to optimize blood glucose levels overnight. Additionally, the method may include monitoring the subject's metabolic markers, such as blood glucose levels, HbA1c, and lipid profiles, to adjust the dosage and combination of highly purified (R)-3'-hydroxybutyl (R)-3'-hydroxybutyrate and anti-diabetic drug for maximum therapeutic efficacy. This approach allows for a personalized treatment plan that addresses the metabolic needs of each subject, potentially improving their overall metabolic health and quality of life.

In some examples, the method for treating metabolic disorders in a subject may involve administering a combination of highly purified (R)-3'-hydroxybutyl (R)-3'-hydroxybutyrate and an anti-diabetic drug, such as metformin, to enhance the therapeutic effects on glucose regulation and insulin sensitivity. The ketone ester may be administered in various forms, including oral capsules, liquid solutions, or transdermal patches, to accommodate different patient preferences and medical needs. In another example, highly purified (R)-3'-hydroxybutyl (R)-3'-hydroxybutyrate may be combined with other anti-diabetic drugs like sulfonylureas or DPP-4 inhibitors, providing a tailored approach to managing different types of diabetes and metabolic conditions. The administration schedule may vary, with some protocols involving daily doses while others may use intermittent dosing to optimize metabolic benefits and minimize potential side effects. Additionally, the method may include monitoring metabolic markers such as blood glucose levels, HbA1c, and lipid profiles to assess the treatment's efficacy and make necessary adjustments. In a further example, the highly purified (R)-3'-hydroxybutyl (R)-3'-hydroxybutyrate and anti-diabetic drug combination may be integrated into a comprehensive treatment plan that includes dietary modifications and physical exercise, thereby promoting overall metabolic health and improving patient outcomes. This approach allows for flexibility in treatment regimens, catering to individual patient needs and enhancing the adaptability of the method within the defined legal and functional scope.

In some examples, the method for improving metabolic health may involve administering a highly purified (R)-3'-hydroxybutyl (R)-3'-hydroxybutyrate composition to a subject and monitoring metabolic markers such as blood glucose levels, insulin sensitivity, and lipid profiles. The highly purified (R)-3'-hydroxybutyl (R)-3'-hydroxybutyrate composition may be formulated in various delivery forms, including oral capsules, liquid solutions, or transdermal patches, to accommodate different patient preferences and medical needs. In another example, the highly purified (R)-3'-hydroxybutyl (R)-3'-hydroxybutyrate composition is combined with dietary interventions, such as a ketogenic diet, to enhance the metabolic benefits. This combination may be tailored to individual metabolic profiles, ensuring personalized treatment plans. Additionally, the method may be adapted to include regular physical activity as part of the regimen, with the highly purified (R)-3'-hydroxybutyl (R)-3'-hydroxybutyrate composition administered pre- or post-exercise to optimize metabolic responses. In a further example, the method incorporates the use of wearable technology to continuously monitor metabolic markers such as glucose levels and ketone concentrations in real-time, providing immediate feedback and allowing for dynamic adjustments to the treatment protocol. This example may also include periodic blood tests to measure more comprehensive metabolic markers, such as HbA1c and inflammatory cytokines, to assess long-term metabolic health improvements. Each of these examples demonstrates the adaptability of the method within the legal and functional scope defined by the patent claims, ensuring a broad application for improving metabolic health in various subject populations.

In some examples, the use of highly purified (R)-3'-hydroxybutyl (R)-3'-hydroxybutyrate may involve a mechanism wherein generated BHB may suppress appetite. BHB may reduce levels of the hunger hormone ghrelin. Reduction in appetite might decrease the risk of obesity and all the diseases associated with obesity-type 2 Diabetes, Cardiovascular Disease, Hypertension, Osteoarthritis, Sleep Apnoea, Non-Alcoholic Fatty Liver Disease. There may be methods of treatment which may include assessment of biomarkers to regulate the treatment, these biomarkers may include in a non-limiting perspective measurement of HbA1C, Fructosamine, serum glucose, C-Reactive Protein (CRP), high-sensitivity CRP (hs-CRP), serum IL-6, TNF-α, Fibrinogen, and D-dimer levels.

In some examples, the use of highly purified (R)-3'-hydroxybutyl (R)-3'-hydroxybutyrate may involve a mechanism wherein generated BHB may suppress levels of lipids in serum. In some examples, BHB may inhibit lipolysis, a process by which fats are broken down into free fatty acids (FFA) and glycerol. This inhibition may occur via the activation of the HCAR2 receptor (also known as GPR109A), which is a G-protein coupled receptor that reduces the activity of the adenylate cyclase/cAMP/PKA signalling pathway. This reduction may lead to decreased lipolytic activity in adipocytes, resulting in lower levels of circulating free fatty acids, which are precursors for triglyceride and cholesterol synthesis. Accordingly, highly purified (R)-3'-hydroxybutyl (R)-3'-hydroxybutyrate supplementation may lower LDL levels. Furthermore, highly purified (R)-3'-hydroxybutyl (R)-3'-hydroxybutyrate supplementation may increase HDL cholesterol in some examples. There may be methods of treatment which may include assessment of biomarkers to regulate the treatment, these biomarkers may include in a non-limiting perspective measurement of triglycerides, LDL, v-LDL, and HDL cholesterol, Apolipoprotein B (ApoB), and Oxidized LDL levels.

In some examples, the use of highly purified (R)-3'-hydroxybutyl (R)-3'-hydroxybutyrate may involve a mechanism wherein generated BHB may prevent liver fat accumulation and Non-Alcoholic Fatty Liver Disease (NAFLD) progression. Excessive accumulation of triacylglycerol (TAG) in NAFLD may be caused by an imbalance between increased hepatic free fatty acids (FFA) uptake and decreased FFA removal via beta-oxidation, lipophagy and exportation via very-low-density lipoprotein. Insulin resistance (IR) may be an important factor in NAFLD because it may increase peripheral fat lipolysis, making FFA available for hepatic uptake. This may enhance hepatic lipogenesis. A master regulator of FFA oxidation in the liver may be the Peroxisome Proliferator-Activated Receptor Alpha (PPARα) nuclear receptor protein. Upon activation, PPARα may stimulate the expression of genes involved in FFA uptake, beta-oxidation and triglyceride turnover. PPARα levels from liver biopsies of NAFLD patients negatively correlate with the severity of steatosis and fibrosis. Conversely, an increase in PPARα was observed after improvement of NAFLD caused by lifestyle modification or bariatric surgery. Accordingly, PPAR agonists may have a use as anti-NAFLD drugs. The activity of PPARα is augmented by its coactivator Peroxisome Proliferator-Activated Receptor Gamma Coactivator 1-alpha (PGC-1α), which may increase expression of mitochondrial fatty acid oxidation enzymes. PGC-1α overexpression may increase hepatic mitochondrial content and decrease hepatic TAG storage and TAG plasma levels. Increased PGC-1α expression may also compensate for the depletion of mitochondrial DNA observed in NAFLD.

Moreover, a ketone ester diet (KED) in particular including ingesting of highly purified (R)-3'-hydroxybutyl (R)-3'-hydroxybutyrate may stimulate mitochondrial biogenesis, increasing PGC-1α expression and increasing the expression of Uncoupling Protein 1 (UCP1), thereby, increasing its metabolic activity. Increasing the metabolic activity of Brown Adipose Tissue (BAT) enhances its ability to uptake succinate and ameliorates NAFLD pathology. Decreasing activity of SUCNR1 by BAT-mediated succinate uptake decreased the expression of inflammatory cytokines like IL-1β, IL-6 and TNFα. BHB also may further decrease NALFD-related inflammation and progression via inhibition of NLRP3 inflammasome which may decrease levels of fibrogenic IL-1β.

In some examples, elevated levels of extracellular succinate may be a pro-inflammatory driver of NAFLD. Succinate Receptor 1 (SUCNR1) may be expressed on the surface of circulating immune cells and also on liver-residing macrophages and on hepatic stellate cells (HSC). The activation of SUCNR1 on HSC by succinate may be an important stimulator of fibrosis. Moreover, activation of SUCNR1 on immune cells may lead to the expression of pro-inflammatory cytokine IL-1β which may promote liver steatosis and fibrosis through the IL-1 receptor. In some examples, liver biopsies may be used to demonstrate that IL-1β is elevated in NAFLD patients and IL-1β mRNA levels may be significantly correlated with Collagen Type I Alpha 1 Chain (COL1A1), a key fibrogenic gene. In some examples, NLRP3 inflammasome may be important in the progression of NAFLD into non-alcoholic steatohepatitis (NASH).

In some examples, reduction of ER stress with highly purified (R)-3'-hydroxybutyl (R)-3'-hydroxybutyrate ingestion may be mediated by increasing the activity of the AMPK-FOXO3 pathway. Activation of AMPK-FOXO3 may result in increased levels of antioxidants mnSOD and catalase. In some examples, highly purified (R)-3'-hydroxybutyl (R)-3'-hydroxybutyrate ingestion may improve insulin signaling and show improved scores of homeostatic model assessment for IR and lower HbAc1. IR may also be improved via weight loss and lifestyle changes. In some examples, BHB may suppress appetite in humans by lowering ghrelin levels which might positively support weight loss efforts.

Amelioration of NAFLD may reduce risk for all-cause mortality and decrease the risk liver diseases including progression to NASH, Liver fibrosis and cirrhosis. There may be methods of treatment with highly purified (R)-3'-hydroxybutyl (R)-3'-hydroxybutyrate which may include assessment of biomarkers to regulate the treatment, these biomarkers may include in a non-limiting perspective, MRI-assessed liver steatosis, measurement of serum levels of tissue inhibitor of metalloproteinases 1, serum levels of cytokeratin 18 fragment levels and fibroblast growth factor 21 levels. There may be other supporting markers such as the standard lipid panel for LDL, HDL, and triglycerides, and measurement of plasma alkaline phosphatase, alanine transaminase, aspartate aminotransferase and albumin.

In some examples, highly purified (R)-3'-hydroxybutyl (R)-3'-hydroxybutyrate ingestion may induce fat browning. Brown adipocytes may oxidize fatty acids due to high mitochondrial density and uncoupled cellular respiration from ATP synthesis which produces heat. Activation of brown fat induces thermogenesis, increases calorie output, and may reduce obesity and other metabolic diseases associated with overconsumption. Fat browning may be induced by highly purified (R)-3'-hydroxybutyl (R)-3'-hydroxybutyrate ingestion to generate BHB by increasing expression of UCP1 protein which is responsible for the uncoupling of cellular respiration and ATP production. Study in rats showed that BHB is capable of inducing fat browning. Fat browning may have clinical relevance to numerous disease state including in a non-limiting perspective obesity type 2 Diabetes, Cardiovascular Disease, Hypertension, Osteoarthritis, Sleep Apnea, Non-Alcoholic Fatty Liver Disease. There may be methods of treatment with highly purified (R)-3'-hydroxybutyl (R)-3'-hydroxybutyrate which may include assessment of biomarkers to regulate the treatment. In some examples, biopsy of adipose tissues may also be possible to assess UCP1 expression. As well, regulation of treatment may include measurements of serum levels of UCP1 itself as well as measurements of serum levels of Fibroblast Growth Factor 21 (FGF21).

Highly Purified (R)-3'-Hydroxybutyl (R)-3'-Hydroxybutyrate and Sarcopenia

In some examples, highly purified (R)-3'-hydroxybutyl (R)-3'-hydroxybutyrate ingestion may ameliorate the symptoms of Sarcopenia, which relates to age-related loss of muscle mass, strength. Ingestion of highly purified (R)-3'-hydroxybutyl (R)-3'-hydroxybutyrate may act by generating BHB which may act through effecting the mTOR pathway. BHB may activate the mTORC1 (mechanistic target of rapamycin complex 1) signaling pathway, which may be important for initiating muscle protein synthesis. mTORC1 may promote the phosphorylation of downstream targets such as p70S6 kinase (p70S6K) and 4E-BP1. The phosphorylation of p70S6K may enhance the translation of mRNAs required for muscle protein synthesis. This cascade may ultimately lead to increased muscle protein synthesis, counteracting muscle loss in sarcopenia. In some examples, the relationship between mTOR activation and sarcopenia may be complex and may lead to different strategies in different cases. Some findings may indicate that while mTORC1 is activated in aging muscle, the effectiveness of this activation in promoting muscle hypertrophy is diminished, leading to the conclusion that low mTOR activation may indeed play a role in sarcopenia. There may be methods of treatment with highly purified (R)-3'-hydroxybutyl (R)-3'-hydroxybutyrate which may include assessment of biomarkers to regulate the treatment, these biomarkers may include in a non-limiting perspective, biopsy related measurement of levels of phosphorylation of p70S6K, p4EBP1 or pS6.

In some examples, highly purified (R)-3'-hydroxybutyl (R)-3'-hydroxybutyrate ingestion may ameliorate the symptoms of Sarcopenia and may act through effecting reduction of inflammation via NF-κB inhibition. In some examples, generated BHB may inhibit the NF-κB (nuclear factor kappa-light-chain-enhancer of activated B cells) signaling pathway, which may be an important mediator of inflammation. NF-κB may typically be activated in response to inflammatory cytokines such as TNF-α and IL-1β. Upon activation, NF-κB may translocate to the nucleus and may promote the transcription of pro-inflammatory genes, including those that encode cytokines, chemokines, and adhesion molecules. By inhibiting NF-κB activation, BHB may reduce the expression of these pro-inflammatory mediators, thus lowering systemic inflammation and preventing muscle wasting that may be exacerbated by chronic inflammation. In some examples, the relationship between mTOR activation and sarcopenia may be complex and may lead to different strategies in different cases. There may be methods of treatment with highly purified (R)-3'-hydroxybutyl (R)-3'-hydroxybutyrate which may include assessment of biomarkers to regulate the treatment, these biomarkers may include in a non-limiting perspective, measurement of serum levels of IL-1beta, IL-6, IL-10, TNF-alpha and CRP.

In some examples, highly purified (R)-3'-hydroxybutyl (R)-3'-hydroxybutyrate ingestion may ameliorate the symptoms of Sarcopenia and may act through mitigation of oxidative stress by generated BHB. BHB may exert antioxidant effects by enhancing the activity of antioxidant enzymes and reducing the production of reactive oxygen species (ROS). It may stimulate the Nrf2 (nuclear factor erythroid 2-related factor 2) pathway, which may lead to the upregulation of various antioxidant proteins such as superoxide dismutase (SOD) and catalase. Nrf2 activation may also reduce oxidative damage to muscle cells by neutralizing ROS, which may be implicated in the pathogenesis of muscle atrophy and sarcopenia. Additionally, BHB may directly scavenge ROS, further protecting muscle tissues from oxidative damage. There may be methods of treatment with highly purified (R)-3'-hydroxybutyl (R)-3'-hydroxybutyrate which may include assessment of biomarkers to regulate the treatment, these biomarkers may include in a non-limiting perspective, measurement of Isoprostanes as a are common plasma markers of lipid oxidation, and 7,8-dihydro-8-oxo-2'-deoxyguanosine as a marker of DNA oxidative damage. In some examples, the biomarkers may include in a non-limiting perspective, thiobarbituric acid reducing substances (TBARS) or 8-Iso-Prostaglandin-F2α (F2-IsoPs).

Highly Purified (R)-3'-Hydroxybutyl (R)-3'-Hydroxybutyrate and Mitochondrial Function In some examples, the method for enhancing mitochondrial function in a subject may involve administering a composition containing highly purified (R)-3'-hydroxybutyl (R)-3'-hydroxybutyrate through oral ingestion. The composition may be formulated as a liquid, capsule, or powder to suit different preferences and improve compliance. The dosage may be adjusted based on the subject's weight, age, and health status to ensure optimal efficacy. In another example, the administration may be via intravenous injection for subjects requiring rapid intervention or those with gastrointestinal absorption issues. The highly purified (R)-3'-hydroxybutyl (R)-3'-hydroxybutyrate may be combined with other mitochondrial enhancers such as Coenzyme Q10 or PQQ (Pyrroloquinoline quinone) to synergistically boost mitochondrial biogenesis. Additionally, the method includes measuring mitochondrial biogenesis markers such as PGC-1α, NRF1, and Transcription Factor A, Mitochondrial (TFAM) in blood or muscle tissue samples to monitor the effectiveness of the treatment. In a further example, the composition may be tailored to include specific nutrients like magnesium and B vitamins that support mitochondrial function, providing a comprehensive approach to enhancing cellular energy production. The method may also incorporate periodic assessments using advanced imaging techniques like MitoTracker staining or electron microscopy to visualize changes in mitochondrial density and morphology, ensuring a thorough evaluation of the treatment's impact.

Highly Purified (R)-3'-Hydroxybutyl (R)-3'-Hydroxybutyrate and Muscle Power Output In some examples, highly purified (R)-3'-hydroxybutyl (R)-3'-hydroxybutyrate ingestion may be useful in maintaining or enhancing muscle power output through generation of BHB. Specifically, ingestion may be of highly purified (R)-3'-hydroxybutyl (R)-3'-hydroxybutyrate, which may be effective in increasing circulating BHB concentrations in the blood plasma, thereby supporting or improving muscle power output.

BHB may be generated when fatty acid levels rise in the body and are metabolized for energy. They have been found to reduce circulating free fatty acids in the plasma, leading to various health benefits, such as improved cognitive performance, and treatment for cardiovascular conditions, diabetes, mitochondrial dysfunctions, and muscle fatigue.

In examples using highly purified (R)-3'-hydroxybutyl (R)-3'-hydroxybutyrate, beneficial factors may include improved taste aspects and high uptake efficiency. In some examples it may be a preferred candidate for achieving significant blood ketone concentrations upon oral ingestion.

In some examples, highly purified (R)-3'-hydroxybutyl (R)-3'-hydroxybutyrate may include a variety of forms, such as liquids, powders, tablets, bars, or granules. These compositions may be ingested either in these forms or mixed with liquids like water, juice, or milk, to achieve the desired ketone levels and muscle power benefits.

In some examples, compositions may also include additional ingredients such as flavors, proteins, carbohydrates, vitamins, and minerals, to enhance desirability for users.

Highly Purified (R)-3'-Hydroxybutyl (R)-3'-Hydroxybutyrate and Cardiovascular Conditions In some examples, the method for treating cardiovascular conditions may involve administering a highly purified (R)-3'-hydroxybutyl (R)-3'-hydroxybutyrate composition in a liquid form, such as a drink or an intravenous solution, to ensure rapid absorption and bioavailability. The composition may include additional ingredients like electrolytes to support cardiovascular health and hydration. In another example, the highly purified (R)-3'-hydroxybutyl (R)-3'-hydroxybutyrate composition is administered in a solid form, such as capsules or tablets, which may be coated to enhance stability and control the release rate of the active ingredient. This form may be particularly useful for long-term treatment regimens. Additionally, the method may include monitoring cardiovascular indicators such as blood pressure, heart rate, and lipid levels through wearable devices that continuously transmit data to healthcare providers. In another example, the highly purified (R)-3'-hydroxybutyl (R)-3'-hydroxybutyrate composition may be administered in combination with cardiovascular medications, such as statins or beta-blockers, to enhance therapeutic efficacy. This combination therapy can be personalized based on the patient's individual cardiovascular health and treatment response. The method may also involve routine blood tests to assess ketone levels and other biomarkers, allowing for adjustments in the dosage and composition of the ketone ester formulation to achieve optimal therapeutic results.

Highly Purified (R)-3'-Hydroxybutyl (R)-3'-Hydroxybutyrate and Muscle Fatigue In some examples, methods for reducing muscle fatigue may involve administering a highly purified (R)-3'-hydroxybutyl (R)-3'-hydroxybutyrate composition to a subject in the form of an orally ingested liquid solution. This liquid solution may be administered as a single dose or in multiple doses throughout the day, depending on the individual's needs and the extent and severity of muscle fatigue. In some examples, the highly purified (R)-3'-hydroxybutyl (R)-3'-hydroxybutyrate composition may be used in a solid form, such as a tablet or capsule, which may be taken with water. This form may be an option for subjects who struggle with liquid supplements or who require a more controlled release of the active ingredients. In some other examples, the highly purified (R)-3'-hydroxybutyl (R)-3'-hydroxybutyrate composition may be combined with other supplements known to support muscle function, such as branched-chain amino acids (BCAAs) or electrolytes, to enhance the effectiveness of the highly purified (R)-3'-hydroxybutyl (R)-3'-hydroxybutyrate composition. The method also includes measuring muscle endurance through various tests, such as isometric strength tests, endurance cycling, or running tests, to monitor the reduction in muscle fatigue over time. In a further example, the highly purified (R)-3'-hydroxybutyl (R)-3'-hydroxybutyrate composition may be administered in conjunction with a structured exercise program tailored to the subject's fitness level and goals, ensuring that the benefits of the ketone ester are enhanced through synergistic effects with physical training. The administration of the highly purified (R)-3'-hydroxybutyl (R)-3'-hydroxybutyrate composition may be adjusted based on the subject's response, with periodic assessments to optimize dosage and timing for optimal outcomes in reducing muscle fatigue.

Highly Purified (R)-3'-Hydroxybutyl (R)-3'-Hydroxybutyrate and Taste Improvement In some examples, the method for improving the taste of a highly purified (R)-3'-hydroxybutyl (R)-3'-hydroxybutyrate composition may involve formulating the composition with natural flavoring agents such as citrus extracts, mint, or berry flavors to mask the bitterness of the ketone ester. This approach may leverage the purified (R),(R)-form enantiomer's reduced bitterness compared to the S-form counterpart, enhancing the overall palatability of the composition. In another example, the highly purified (R)-3'-hydroxybutyl (R)-3'-hydroxybutyrate composition is combined with a sweetening agent like stevia or monk fruit extract, which not only improves the taste but also maintains the composition's low-calorie profile, making the composition suitable for health-conscious consumers. Additionally, the composition may be encapsulated in a gel capsule to minimize direct taste exposure, providing an alternative delivery method for those sensitive to the taste. Furthermore, the highly purified (R)-3'-hydroxybutyl (R)-3'-hydroxybutyrate composition may be integrated into a beverage formulation, such as a sports drink or a smoothie, where the flavors and textures of other ingredients help to further mask any residual bitterness, thereby enhancing the overall consumer experience. Each of these examples ensures that the highly purified (R)-3'-hydroxybutyl (R)-3'-hydroxybutyrate composition may remain effective while significantly improving the taste, making the composition more appealing and easier to consume for a broader audience.

General Summary of Clinical Relevance of Ingestion of Highly Purified (R)-3'-Hydroxybutyl (R)-3'-Hydroxybutyrate As has been mentioned, there may be numerous benefits of ingesting highly purified compositions of (R)-3'-hydroxybutyl (R)-3'-hydroxybutyrate. In summary, these benefits may include metabolic benefits including but not limited to enhanced fat oxidation and weight loss, improved insulin sensitivity, increased metabolic flexibility, amelioration of metabolic syndrome, neurological benefits, neuroprotective effects against neurodegenerative diseases, improved cognitive function and memory. Other benefits may include treatment aspects for epilepsy and seizure disorders, improvements for mood and mood stabilization, cardiovascular benefits, reduced inflammation in cardiovascular tissues, improvement in lipid profiles, reduction in blood pressure, anti-inflammatory effects, systemic reduction of inflammatory markers, treatment for inflammatory disorders, improvements in energy production, improvements as an alternative energy source for brain and muscles, enhanced physical endurance and performance, improved cellular health, promotion of mitochondrial biogenesis, improvement in anti-aging effects at the cellular level, improvements in gut health, beneficial effects on gut microbiome composition, improvement in intestinal barrier function, improved anti-tumor effects in some cancer models, improvements in bone health, improvements in bone mineral density, improvements in the immune system, enhancement in immune system function, reduction in oxidative stress, antioxidant-like effects in various tissues, improvements in hormonal regulation, improved influence on hunger and satiety hormones, improved recovery from exercise, reductions in exercise-induced muscle damage, and improvements in respiratory function. Additional aspects may include benefits in respiratory conditions, improved protections for renal function, improved protective effects against kidney injury, improved liver health, reduction in liver fat accumulation, and improvements in reproductive health including benefits in some fertility issues. In some additional examples, additional aspects may include improvements in sleep quality, improvement in sleep patterns and quality, improved resilience to stress, enhancement of cellular stress resistance mechanisms, improvements in wound healing with acceleration of wound healing processes, and improvements in longevity with potential contribution to increased lifespan.

In some examples, the dosing of highly purified forms of (R)-3'-hydroxybutyl (R)-3'-hydroxybutyrate may be set at a level between 3 and 150 gm/day. In still further examples, particularly for treatment protocols which may be sensitive to standard levels of impurities, doses may be between 0 and 300 gm/day. In some treatment protocols, a dose may be adjusted based on the mass of a patient being treated. Accordingly, targets for dosing may be set for particular per kg of body mass dose levels which may range between 0.01 and 4 gm/kg body mass/day as non-limiting examples.

A number of embodiments of the present disclosure have been described. While this specification contains many specific implementation details, there should not be construed as limitations on the scope of any disclosures or of what may be claimed, but rather as descriptions of features specific to particular embodiments of the present disclosure. While embodiments of the present disclosure are described herein by way of example using several illustrative drawings, those skilled in the art will recognize the present disclosure is not limited to the embodiments or drawings described. It should be understood the drawings, and the detailed description thereto are not intended to limit the present disclosure to the form disclosed, but to the contrary, the present disclosure is to cover all modification, equivalents and alternatives falling within the spirit and scope of embodiments of the present disclosure as defined by the appended claims.

The headings used herein are for organizational purposes only and are not meant to be used to limit the scope of the description or the claims. As used throughout this application, the word "may" be used in a permissive sense (i.e., meaning having the potential to), rather than the mandatory sense (i.e., meaning must). Similarly, the words "include," "including," and "includes" mean including but not limited to. To facilitate understanding, reference numerals have been used, where possible, to designate like elements common to the figures.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising," "including," and "having" can be used interchangeably.

Certain features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while method steps may be depicted in the drawings in a particular order, this should not be understood as requiring that such operations be performed in the particular order shown or in a sequential order, or that all illustrated operations be performed, to achieve desirable results.

What is claimed is:

1. A method for producing enantiomerically purified (R)-3'-hydroxybutyl (R)-3'-hydroxybutyrate monoester, comprising:

(a) providing enantiomerically purified (R)-1,3-butanediol and enantiomerically purified ethyl (R)-3-hydroxybutyrate;

(b) combining the (R)-1,3-butanediol and ethyl (R)-3-hydroxybutyrate in a reaction comprising a *Candida antarctica* lipase B immobilized on an acrylic resin support in a hydrophobic organic solvent selected from heptane, toluene, methyl tert-butyl ether, tert-amyl alcohol, and combinations thereof;

(c) incubating the mixture in the hydrophobic organic solvent at a temperature of about 25° C. to 50° C. and a pressure of about 0 to 759 mm Hg, while continuously removing ethanol byproduct via a vacuum takeoff and condenser under reduced pressure, wherein molecular sieves are included to maintain low water activity and preserve stereochemical integrity during transesterification;

(d) filtering a reaction mixture to remove the immobilized *Candida antarctica* lipase B and the water-scavenging solids;

(e) subjecting the filtrate to reduced-pressure distillation to remove ethanol, solvent, and unreacted starting materials, wherein unreacted ethyl (R)-3-hydroxybutyrate is recovered in a designated distillation cut for recycling;

(f) purifying the resulting intermediate by wiped-film evaporation comprising: (i) a first pass configured to remove residual light ends; and (ii) a second pass operated at lower absolute pressure to selectively target and remove S-form, and collect the enantiomerically purified (R)-3'-hydroxybutyl (R)-3'-hydroxybutyrate monoester as a main product cut;

(g) determining a purity level of the enantiomerically purified (R)-3'-hydroxybutyl (R)-3'-hydroxybutyrate monoester; and (h) repeating one or more of steps (e), (f), and (g) if required until obtaining the enantiomerically purified (R)-3'-hydroxybutyl (R)-3'-hydroxybutyrate monoester at a purity of at least 95%;

wherein process conditions are selected to preserve enantiomeric integrity and minimize racemization during volatility-based separations.

2. The method of claim 1, wherein a threshold of step (h) requires the enantiomerically purified (R)-3'-hydroxybutyl (R)-3'-hydroxybutyrate monoester to be present at a purity of at least 99%.

3. The method of claim 2, wherein a removal of at least a first impurity results in a reduction of exposure of said first impurity to a user, wherein the first impurity is associated with an undesirable side effect.

4. The method of claim 1, wherein the immobilized *Candida antarctica* lipase B is washed with a non-denaturing solvent between cycles.

5. The method of claim 1, wherein the hydrophobic organic solvent is selected from the group consisting of heptane, toluene, methyl tert-butyl ether, and tert-amyl alcohol, wherein the hydrophobic organic solvent comprises heptane.

6. The method of claim 1, wherein a molar ratio of the (R)-1,3-butanediol to the ethyl (R)-3-hydroxybutyrate is from about 1:1 to about 1.2:1.

7. The method of claim 1, wherein enzyme loading is from about 1% to about 25% by weight, relative to a total reaction mass in a presence of the molecular sieves configured to maintain the low water activity.

8. The method of claim 1, wherein a reaction is monitored by gas chromatography and/or mass spectrometry to determine conversion and chiral high-performance liquid chromatography is employed to verify enantiomeric excess at each stereocenter.

9. The method of claim 1, wherein the purity of the enantiomerically purified (R)-3'-hydroxybutyl (R)-3'-hydroxybutyrate monoester is confirmed by chiral high-performance liquid chromatography.

10. The method of claim 1, wherein the wiped-film evaporation comprises at least two passes, with the first pass to remove light ends and the second pass to collect the enantiomerically purified (R)-3'-hydroxybutyl (R)-3'-hydroxybutyrate monoester as a main product cut, wherein higher-boiling materials including diester and polycondensed species are routed to a tails stream.

11. The method of claim 1, further comprising recycling unreacted (R)-1,3-butanediol and ethyl (R)-3-hydroxybutyrate for use in subsequent reactions, wherein solvent is recovered by the reduced-pressure distillation and returned to service via a solvent recycle loop.

12. The method of claim 1, wherein the process is conducted in a continuous flow reactor containing the immobilized *Candida antarctica* lipase B and configured for continuous ethanol removal via the vacuum takeoff and the condenser.

13. The method of claim 1, wherein the immobilized *Candida antarctica* lipase B is washed with a non-denaturing solvent and dried under nitrogen between reaction cycles prior to reuse.

14. The method of claim 1, wherein the wiped-film evaporation is operated under conditions selected to minimize racemization.

15. The method of claim 1, further comprising an intermediate high-performance liquid chromatography operation for verification of enantiomeric excess at each stereocenter for additional purification of the enantiomerically purified (R)-3'-hydroxybutyl (R)-3'-hydroxybutyrate monoester.

16. The method of claim 1, wherein the enantiomerically purified (R)-3'-hydroxybutyl (R)-3'-hydroxybutyrate monoester composition is formulated as a liquid, powder, or capsule.

17. The method of claim 1, wherein the enantiomerically purified (R)-3'-hydroxybutyl (R)-3'-hydroxybutyrate monoester is produced with an enantiomeric excess of at least 99% prior to incorporation into a formulation comprising additional components, wherein the low water activity and continuous ethanol removal are maintained during the transesterification to preserve the stereochemical integrity.

* * * * *